United States Patent
Zheng et al.

(10) Patent No.: US 9,365,504 B2
(45) Date of Patent: Jun. 14, 2016

(54) SALTS OF KUKOAMINE B, PREPARATION METHOD AND USE THEREOF

(75) Inventors: Jiang Zheng, Chongqing (CN); Xinchuan Zheng, Chongqing (CN); Xin Liu, Chongqing (CN); Hong Zhou, Chongqing (CN); Ning Wang, Chongqing (CN); Hongwei Cao, Chongqing (CN); Yan Li, Chongqing (CN); Yongling Lu, Chongqing (CN); Kecen Zhao, Chongqing (CN); Jingcheng Yang, Chongqing (CN); Yang Yang, Chongqing (CN); Yuanfeng Zhu, Chongqing (CN); Guo Wei, Chongqing (CN); Min Huang, Chongqing (CN)

(73) Assignees: THE FIRST AFFILIATED HOSPITAL, THIRD MILITARY UNIVERSITY, PLA, Chongqing (CN); TIANJIN CHASESUN PHARMACEUTICAL CO., LTD., Tianjin (CN)

( * ) Notice: Subject to any disclaimer, the term of this patent is extended or adjusted under 35 U.S.C. 154(b) by 361 days.

(21) Appl. No.: 13/884,558

(22) PCT Filed: Mar. 21, 2011

(86) PCT No.: PCT/CN2011/000479
§ 371 (c)(1),
(2), (4) Date: Jul. 2, 2013

(87) PCT Pub. No.: WO2012/062026
PCT Pub. Date: May 18, 2012

(65) Prior Publication Data
US 2013/0289112 A1    Oct. 31, 2013

(30) Foreign Application Priority Data

Nov. 10, 2010 (CN) .......................... 2010 1 0539028

(51) Int. Cl.
| C07C 37/02 | (2006.01) |
|---|---|
| C07C 235/34 | (2006.01) |
| C07C 309/04 | (2006.01) |
| C07C 53/08 | (2006.01) |
| C07C 55/10 | (2006.01) |
| C07C 59/08 | (2006.01) |
| C07C 59/245 | (2006.01) |
| C07C 59/255 | (2006.01) |
| C07C 53/10 | (2006.01) |
| C07C 57/145 | (2006.01) |
| C07C 229/24 | (2006.01) |
| C07C 309/30 | (2006.01) |
| C07C 53/122 | (2006.01) |
| C07C 53/124 | (2006.01) |
| C07C 55/06 | (2006.01) |
| C07C 55/08 | (2006.01) |
| C07C 55/14 | (2006.01) |
| C07C 57/15 | (2006.01) |
| C07C 57/44 | (2006.01) |
| C07C 59/265 | (2006.01) |
| C07C 59/50 | (2006.01) |
| C07C 63/06 | (2006.01) |
| C07C 309/25 | (2006.01) |

(52) U.S. Cl.
CPC ............... *C07C 309/04* (2013.01); *C07C 53/08* (2013.01); *C07C 53/10* (2013.01); *C07C 53/122* (2013.01); *C07C 53/124* (2013.01); *C07C 55/06* (2013.01); *C07C 55/08* (2013.01); *C07C 55/10* (2013.01); *C07C 55/14* (2013.01); *C07C 57/145* (2013.01); *C07C 57/15* (2013.01); *C07C 57/44* (2013.01); *C07C 59/08* (2013.01); *C07C 59/245* (2013.01); *C07C 59/255* (2013.01); *C07C 59/265* (2013.01); *C07C 59/50* (2013.01); *C07C 63/06* (2013.01); *C07C 229/24* (2013.01); *C07C 235/34* (2013.01); *C07C 309/25* (2013.01); *C07C 309/30* (2013.01)

(58) Field of Classification Search
CPC ............................ C07C 37/002; C07C 235/34
See application file for complete search history.

(56) References Cited

U.S. PATENT DOCUMENTS

2013/0172421 A1* 7/2013 Zheng et al. .................. 514/616

FOREIGN PATENT DOCUMENTS

| CN | 201010156503.X |   | 4/2010 |
| CN | 101829075 A | * | 9/2010 |

OTHER PUBLICATIONS

Yingyongnarongkul et al, Arch. Pharm. Res., vol. 31, No. 6, 698-704, 2008.*
George Karigiannis et al. Simple fragment syntheses of all four isomers of the spermine alkaloid kukoamine. Tetrahedron Letters. vol. 39 No. 28. 1998, pp. 5117-5120.
Shinji Funayama, et al. Kukoamine B, a spermine alkaloid from Lycium chinense, Phytochemistry, vol. 38 No. 6. 1995. pp. 1529-1531.

* cited by examiner

*Primary Examiner* — Jeffrey S Lundgren
*Assistant Examiner* — Chris Simmons
(74) *Attorney, Agent, or Firm* — Patterson Thuente Pedersen, P.A.

(57) ABSTRACT

Salts of kukoamine B, their preparation method and their pharmaceutical use in preparation of drugs for preventing and treating sepsis. Experiments indicate that salts of kukoamine B have a good effect on antagonizing the key factors inducing sepsis, and can be used in the preparation of drugs for preventing and treating sepsis. Under the current circumstances of the lack of effective measures for the treatment of sepsis in clinical practice, the medicinal formulations, which comprise the salts of kukoamine B, pharmaceutically acceptable carrier and/or diluent, provide a new approach for the prevention and treatment of sepsis.

1 Claim, 7 Drawing Sheets

A

B

E

F

G

H

SALTS OF KUKOAMINE B, PREPARATION METHOD AND USE THEREOF

PRIORITY CLAIM

The present application is a National Phase entry of PCT Patent Application No. PCT/CN2011/000479, filed Mar. 21, 2011, which claims priority from CN Patent Application No. 201010539028.4, filed Nov. 10, 2010, which applications are incorporated by reference herein in their entirety.

FIELD OF THE INVENTION

The present invention relates to the field of pharmaceutical technology, particularly to the salts of kukoamine B, their preparation method and their pharmaceutical use in preparation of drugs for preventing and treating sepsis.

BACKGROUND OF THE INVENTION

Sepsis, also known as systemic inflammatory response syndrome (SIRS) induced by infection, is a common complication of burn injury, trauma, tumor and infectious diseases, and now has been globally recognized as the leading cause of mortality in intensive care units (ICU). The existing principal clinical treatments of sepsis are initial antibiotic administration and remedy of hypoxic ischemic damage, which adopt conventional treatments of organ failure and shock, and there is no specific treatment for it up to now. Usually, medication to sepsis empirically adopts non-specific drugs, e.g. glucocorticoids, insulin, immunomodulator, etc., but their curative effect is still uncertain. In the 1990s, anti-lipid A monoclonal antibody HA-1A (Centoxin) was used in the treatment of sepsis after burn injury and trauma in the US Army during the Gulf War. Centoxin also was clinically used in some European country and Japan. However due to its possible adverse effect to septic shock, Centoxin failed to obtain approval by US Food and Drug Administration (FDA) in 1992 and then disappeared from the European market as well. Recombinant human activated protein C (rhAPC) is the only drug approved by FDA for sepsis treatment so far (tradename XIGRIS). Result of clinical trial shows that rhAPC, which obtain FDA marketing approval in November 2011, can reduce the 28-day mortality of patients suffering sepsis. However, result of the second clinical trial shows that there is no difference in 28-day mortality between the rhAPC group and the control group. In another clinical trial in 2007, rhAPC exhibits not only no effect in increasing the survival rate of patients suffering sepsis, but also the adverse effect of inducing severe bleeding tendency in patients. Therefore, the organizing institution of this clinical trial does not recommend rhAPC as clinical drug for sepsis treatment.

The discovery of pathogen-associated molecular patterns (PAMPs) and pattern recognition receptors (PRRs) thereof have produced a qualitative upgrade on knowledge of sepsis. It has been proven that the pathogenesis of sepsis is that the PAMPs (including lipopolysaccharide/endotoxin (LPS), bacterial genomic DNA (CpG DNA), and peptideglycan (PGN)) of pathogens are recognized by corresponding PRRs in the membranes of or intracellular of inflammatory cells in non-specific immune system after the invasion of pathogens into organism, which process will cause inflammatory cells to be activated and release inflammatory mediators, resulting systemic inflammatory response and then organ damage. Because of the failure of existing treatments, e.g. antagonizing the important effector molecules in inflammatory response, correction of the disorders of coagulation and complement system, and antagonizing LPS alone, searching for drugs which could antagonize multiple major PAMPs (LPS, CpG DNA, PGN, etc.) concurrently and blocking the onset of sepsis at the source may bring a breakthrough on the sepsis treatment.

Kukoamine B is a naturally existing alkaloid isolating from *Lycii cortex.*, one kind of traditional Chinese herbs, the chemical structure of which is as follows:

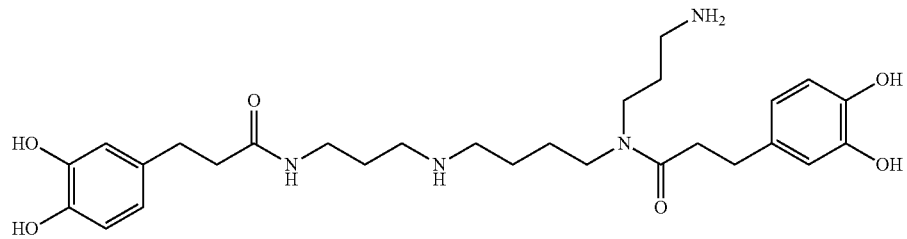 [SMILES: NCCCN(CCCCNCCCNC(=O)CCc1ccc(O)c(O)c1)C(=O)CCc1ccc(O)c(O)c1]

Kukoamine B, which exists in the form of free alkali, was first isolated from *Lycii cortex.* by Shinji Funayama of Japan in 1995 (S. Funayama, G. Zhang & S. Nozoe. Phytochemistry. 1995; 38: 1529-1531). There is no research about biological activity of kukoamine B reported, other than methods of extraction, isolation, purification and structural characterization thereof The use of kukoamine B in the preparation of drugs for the prevention and treatment of sepsis and autoimmune disease has been disclosed in the earlier Chinese patent application filed by applicant (Chinese patent application No. 201010156503.X).

The difference among kukoamine B contents in various *Lycii cortex.* from different habitats and picking time is comparatively large. Therefore, extraction, isolation and purification of kukoamine B from plants for the preparation of drugs for preventing and treating sepsis have such defects as instability in source, high production costs and high energy consumption. Chemical synthesis may provide a new method for the preparation of kukoamine B. However, no research on total chemical synthesis of kukoamine B was found so far after reviewing previous researches and patents.

As compared with naturally occurring kukoamine B, salts of kukoamine B exists in the form of salt and has a new chemical structure. The total chemical synthesis method of salts of kukoamine B has not been disclosed that the applicants are aware of by any patents and literatures so far. Until now, there is also no report that the applicants are aware of about the use of salts of kukoamine B in the treatment of sepsis, particularly through antagonizing multiple PAMPs (LPS and CpG DNA) concurrently.

SUMMARY OF THE INVENTION

Aiming at the problems mentioned above, embodiments of the present invention provide salts of kukoamine B and a preparation method thereof, as well as the use of salts of kukoamine B and pharmaceutical compositions containing them in preparation of drugs for preventing and treating sepsis. Using salts of kukoamine B and pharmaceutical compositions containing them for sepsis treatment has a novel mechanism of action, reliable curative effect and safety, and provides a new approach for the treatment of sepsis.

The technical solutions of embodiments of the present invention are as follows: The chemical structure of salts of kukoamine B is as follows:

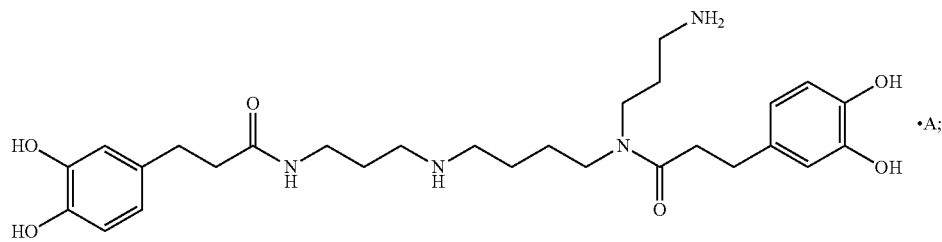 [SMILES: NCCCN(CCCCNCCCNC(=O)CCc1ccc(O)c(O)c1)C(=O)CCc1ccc(O)c(O)c1]

wherein A can comprise an inorganic acid, including, for example, hydrogenacids and/or oxacids, or an organic acid, including, for example, carboxylic acids, hydroxy acids, sulfoacids and/or acidic amino acids.

The salts of kukoamine B are acid salts, which are formed by the basic group in the molecular structure of kukoamine B, including inorganic acid salts and organic acid salts.

In some embodiments, A comprises a hydrogenacid, wherein the hydrogenacid is any one of hydrochloric acid and hydrobromic acid.

In some embodiments, A comprises an oxacid, wherein the oxacid is any one of sulfuric acid, phosphoric acid, and nitric acid.

In some embodiments, A comprises an inorganic acid, wherein the inorganic acid is any one of hydrochloric acid, hydrobromic acid, sulfuric acid, and phosphoric acid.

In some embodiments, A comprises a carboxylic acid, wherein the carboxylic acid is any one of acetic acid, propionic acid, butyric acid, oxalic acid, malonic acid, succinic acid, adipic acid, benzoic acid, phenylpropionic acid, cinnamic acid, stearic acid, trifluoroacetic acid, maleic acid, fumaric acid, nicotinic acid, and palmitic acid.

In some embodiments, A comprises a hydroxy acid, wherein the hydroxy acid is any one of malic acid, citric acid, lactic acid, hydroxybutyric acid, lactobionic acid, tartaric acid, mandelic acid, gluconic acid, glucuronic acid, and ascorbic acid.

In some embodiments, A comprises a sulfoacid, wherein the sulfoacid is any one of methanesulfonic acid, benzenesulfonic acid, p-toluenesulfonic acid, and camphorsulfonic acid.

In some embodiments, A comprises an acidic amino acid, wherein the acidic amino acid is any one of glutamic acid and aspartic acid.

In some embodiments, A comprises an organic acid, wherein the organic acid is any one of acetic acid, maleic acid, succinic acid, malic acid, lactic acid, tartaric acid, methanesulfonic acid, p-toluenesulfonic acid, glutamic acid, and aspartic acid.

According to embodiments, the acids in salts of kukoamine B are selected from a variety of inorganic acids and/or organic acids. Hereinafter, two or three representative acids are selected from each category of pharmaceutically acceptable acids for illustrating common problems in the preparation of salts of kukoamine B, including: hydrochloric acid and hydrobromic acid selected from inorganic hydrogenacid; sulfuric acid and phosphoric acid selected from inorganic oxacid; acetic acid, maleic acid and succinic acid selected from organic carboxylic acids; malic acid, lactic acid and tartaric acid selected from organic hydroxy acids; methanesulfonic acid and p-toluenesulfonic acid selected from organic sulfoacid; glutamic acid and aspartic acid selected from organic acidic amino acids. Although the experiments of embodiments of the present invention only show the results from the four inorganic acids and ten organic acids mentioned above, other inorganic acids and/or organic acids (including acids exemplified or not exemplified herein) can be used in the preparation of salts of kukoamine B in the same manner.

The drugs made from salts of kukoamine B and pharmaceutical compositions containing them for the prevention and treatment of sepsis can be taken through gastrointestinal drug delivery in the dosage form like powders, tablets, granules, capsules, solutions, emulsions, suspensions, etc.; or through parenteral drug delivery by injection administration, intracavity administration, transmucosal administration, etc. The optimal dosages for adults are 0.1-15 mg per kilogram of body weight per day, and the administration can be made one or more times per day.

The salts of kukoamine B are prepared through a series of chemical synthesis with 3,4-Dimethoxyhydrocinnamic acid (or 3,4-Dihydroxyphenyl Propionic acid) and butanediamine as reactants, and in one embodiment, particularly as follows:

(1) Reaction is carried out by compound I having the following structural formula I with hydrobromic acid at 100-160° C., to generate compound II, and the stoichiometric ratio of compound I to hydrobromic acid is 1:2-5;

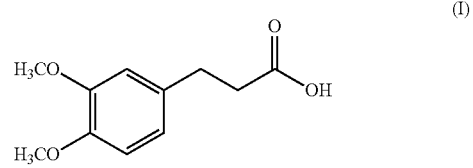

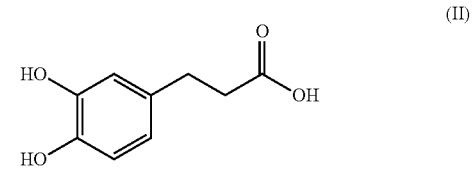

(2) Compound II is dissolved in N,N-dimethylformamide to make the reaction system be in the N,N-dimethylformamide solution environment; and then potassium carbonate and benzyl chloride are added; the reaction is carried out at 60-100° C. to generate compound III; the stoichiometric ratio of compound II: potassium carbonate:benzyl chloride is 1:3-6:3-5;

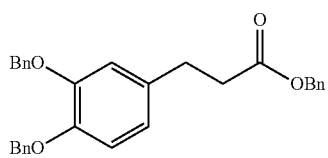

(III)

(3) Compound III is added into sodium hydroxide solution; then methanol is added to make the reaction system be in the methanol solution environment; the reaction is carried out at 40-90° C. to generate compound IV; the stoichiometric ratio of compound III to sodium hydroxide is 1:1-3;

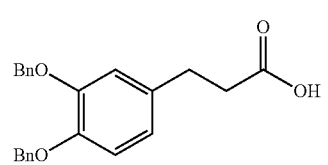

(IV)

(4) Compound IV is dissolved in dichloromethane and then added with N,N-dimethylformamide to make the reaction system be in environment of mixed solution containing N,N-dimethylformamide and dichloromethane; then thionyl chloride is added; the reaction is carried out at 45-65° C. to generate compound V; the stoichiometric ratio of compound IV to thionyl chloride is 1:1-2;

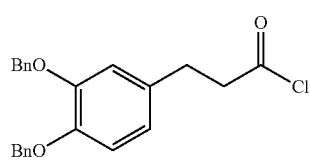

(V)

(5) Compound VI is added with sodium hydroxide solution and then added with ethanol solution of Di-tert-butyl dicarbonate; the reaction is carried out at room temperature to generate compound VII; the stoichiometric ratio of sodium hydroxide:compound VI:Di-tert-butyl dicarbonate is 1-2:1:0.5-1;

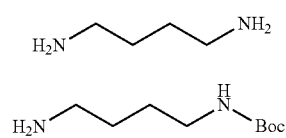

(VI)

(VII)

(6) Compound VII is dissolved in methanol to make the reaction system be in the methanol solution environment, and then added with methanol solution of acrylon; the reaction is carried out at room temperature to generate compound VIII; the stoichiometric ratio of compound VII to acrylon is 1:1-2;

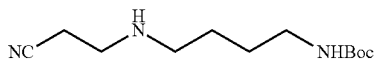

(VIII)

(7) Compound VIII is added with tetrahydrofuran and triethylamine to make the reaction system be in an environment of mixed solution containing tetrahydrofuran and triethylamine, and then added with tetrahydrofuran solution of benzyl chloroformate; the reaction is carried out at room temperature to generate compound IX; the stoichiometric ratio of compound VIII to benzyl chloroformate is 1:1-2;

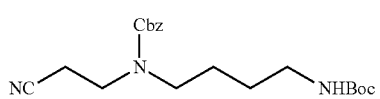

(IX)

(8) Compound IX is put into an autoclave, and added with saturated methanol solution of ammonia until compound IX is completely dissolved; and then, Raney nickel, the mass of which is equivalent to 10-50% of the compound IX, is added into the reaction solution; aeration is applied to ensure the reaction system in hydrogen under 1-10 MPa; the reaction is carried out at 35-50° C. to generate compound X;

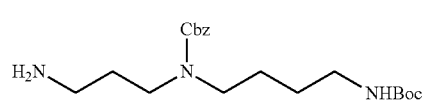

(X)

(9) Compound X is dissolved in dichloromethane, and then added with triethylamine to make the reaction system be in an environment of mixed solution containing dichloromethane and triethylamine; then, the dichloromethane solution of compound V is added into reaction solution at a temperature below 0° C.; the reaction generates compound XI; the stoichiometric ratio of compound X to compound V is 1:1-1.5;

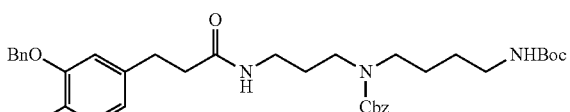

(XI)

(10) Compound XI is dissolved in dichloromethane to make the reaction system be in the dichloromethane environment, and then added with trifluoroacetic acid; the reaction is carried out at room temperature to generate compound XII; the stoichiometric ratio of compound XI to trifluoroacetic acid is 1:2-5;

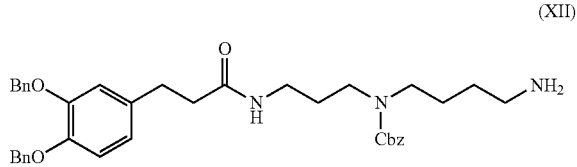 [SMILES: NCCCCN(CCCNC(=O)CCc1ccc(OCc2ccccc2)c(OCc2ccccc2)c1)C(=O)OCc1ccccc1]

(XII)

(11) Compound XII is dissolved in methanol, and then added with triethylamine to make the reaction system be in an environment of mixed solution containing methanol and triethylamine; the reaction system is heated to 50-80° C. and added with methanol solution of acrylon; the reaction solution is cooled down to room temperature to carry out the reaction, which generates compound XIII; the stoichiometric ratio of compound XII to acrylon is 1:1-2;

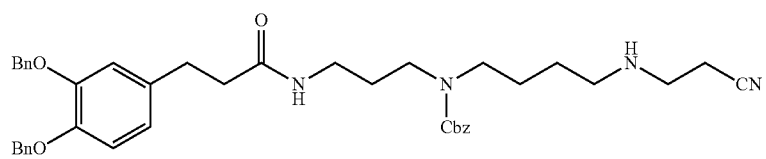

(XIII)

(12) Compound XIII is dissolved in dichloromethane, and then added with triethylamine to make the reaction system be in an environment of mixed solution containing dichloromethane and triethylamine; the dichloromethane solution of compound V is added into the reaction system at a temperature below 0° C.; the reaction generates compound XIV;

the stoichiometric ratio of compound XIII to compound V is 1:1-1.5;

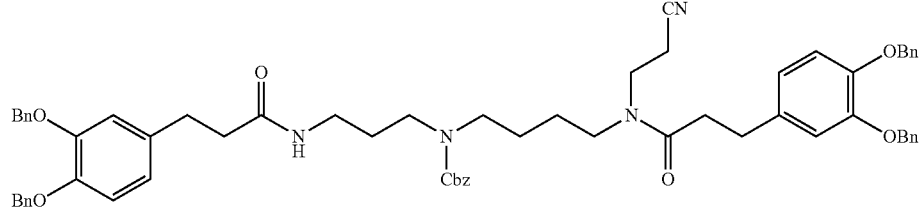

(XIV)

(13) Compound XIV is put into an autoclave, and added with mixed solution containing saturated methanol solution of ammonia and tetrahydrofuran until compound XIV is completely dissolved, such that the reaction system is in an environment of solution thereof; and then, Raney nickel, the mass of which is equivalent to 10-50% of the compound XIV, is added into the reaction system; aeration is applied to ensure the reaction system in hydrogen under 1-10 MPa; the reaction is carried out at 35-50° C. to generate compound XV;

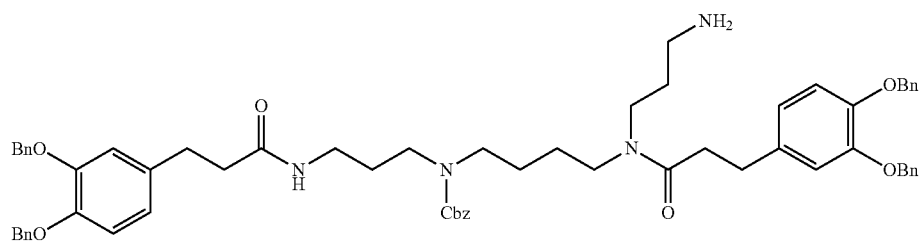

(XV)

(14) Compound XV and any one of the above-mentioned acids are put into an autoclave, and added with mixed solution containing methanol, tetrahydrofuran and water until compound XV is completely dissolved, such that the reaction system is in an environment of solution thereof; and then, Pd/C (palladium-carbon catalyst), the mass of which is equivalent to 10-30% of the compound XV, is added into the reaction system; aeration is applied to ensure the reaction system in hydrogen under 1-10 MPa; the reaction is carried out at 25-45° C. to generate salt of kukoamine B; the stoichiometric ratio of compound XV to acid is 1:1-8.

Experiments conducted by the applicant demonstrate that the above-mentioned synthetic reaction may yield 15% salts of kukoamine B.

The pharmaceutical compositions of salts of kukoamine B according to embodiments of the present invention, including the above-mentioned salts of kukoamine B, include salts of kukoamine B as an active ingredient and a pharmaceutically acceptable carrier and/or diluent.

The salts of kukoamine B, and pharmaceutical composition of salts of kukoamine B, according to embodiments of the present invention can be used in the preparation of drugs for preventing and treating sepsis.

Through pharmacological testing, the applicant demonstrates that:

(1) Salts of kukoamine B could bind with lipid A, the active center of LPS;

(2) Salts of kukoamine B could neutralize LPS in vitro in a dose dependent manner;

(3) Salts of kukoamine B could respectively inhibit the release of inflammatory mediators in RAW 264.7 cells induced by LPS and CpG DNA in a dose dependent manner.

The action mechanism of using salts of kukoamine B and the pharmaceutical compositions containing them for preventing and treating sepsis according to embodiments of the present invention is novel, i.e. concurrently antagonizing the multiple PAMPs inducing sepsis, and different from drugs such as glucocorticoids, insulin, drugs antagonizing inflammatory mediators, anticoagulant, polypeptide antagonizing LPS, and monoclonal antibody antagonizing lipid A. By means of concurrently antagonizing multiple pathogen-associated molecules, the salts of kukoamine B and the pharmaceutical compositions containing them can significantly inhibit the inflammatory response induced by them, to thereby have an effect and to provide a new measure for the prevention and treatment of sepsis.

Embodiments of the present invention select many kinds of inorganic acids and/or organic acids for the description of common problems in the preparation of salts of kukoamine B. However, it is to be understood by those skilled in the art that salts of kukoamine B can be prepared from similar inorganic acids and/or organic acids by methods well known in the art. It is also to be understood by those skilled in the art that kukoamine B can be extracted, isolated and purified from plants by conventional methods of phytochemistry. Therefore, it should be noted that variations and modifications can be made on the aforementioned preparation methods without departing from the concepts of the present invention. For example, the inorganic acids and/or organic acids mentioned above can be replaced by other inorganic acids and/or organic acids, and structural modification can be made to the kukoamine B, whether natural or synthetic, based on the concepts of embodiments of the present invention. Any variations and modifications made to the present invention by those skilled in the art under the enlightenment of the description fall within the scope of the claims of the present invention.

BRIEF DESCRIPTION OF THE DRAWINGS

FIG. 1A shows the results of kukoamine B malate, kukoamine B succinate, kukoamine B lactate, kukoamine B tartrate, kukoamine B methanesulfonate, kukoamine B hydrochlorate, and kukoamine B sulfate; and FIG. 1B shows the results of kukoamine B p-toluenesulfonate, kukoamine B glutamate, kukoamine B acetate, kukoamine B maleate, kukoamine B aspartate, kukoamine B hydrobromide, and kukoamine B phosphate.

FIG. 2A shows the results of kukoamine B malate, kukoamine B succinate, kukoamine B lactate, kukoamine B tartrate, kukoamine B methanesulfonate, kukoamine B hydrochlorate, and kukoamine B sulfate; and FIG. 2B shows the results of kukoamine B p-toluenesulfonate, kukoamine B glutamate, kukoamine B acetate, kukoamine B maleate, kukoamine B aspartate, kukoamine B hydrobromide, and kukoamine B phosphate.

FIGS. 3A, 3B, 3C, 3D, 3E, 3F, 3G, 3H, 3I and 3J show the results of kukoamine B malate, kukoamine B succinate, kukoamine B lactate, kukoamine B tartrate, kukoamine B methanesulfonate, kukoamine B p-toluenesulfonate, kukoamine B glutamate, kukoamine B acetate, kukoamine B hydrochlorate, and kukoamine B sulfate, respectively.

FIGS. 4A, 4B, 4C, 4D, 4E, 4F, 4G, 4H, 4I and 4J show the results of kukoamine B malate, kukoamine B succinate, kukoamine B lactate, kukoamine B tartrate, kukoamine B methanesulfonate, kukoamine B p-toluenesulfonate, kukoamine B glutamate, kukoamine B acetate, kukoamine B hydrochlorate, and kukoamine B sulfate, respectively.

DETAILED DESCRIPTION OF EMBODIMENTS

Figure 1:
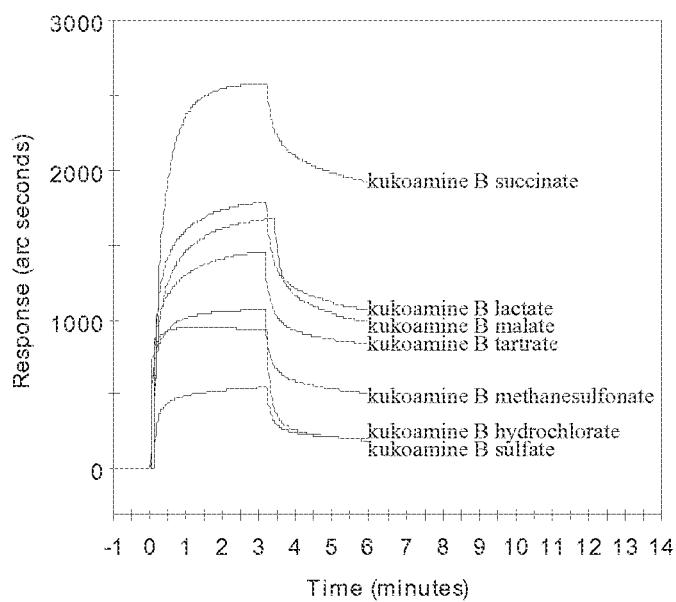
FIG. 1 shows the binding reaction of salts of kukoamine B with lipid A.
Figure 1:
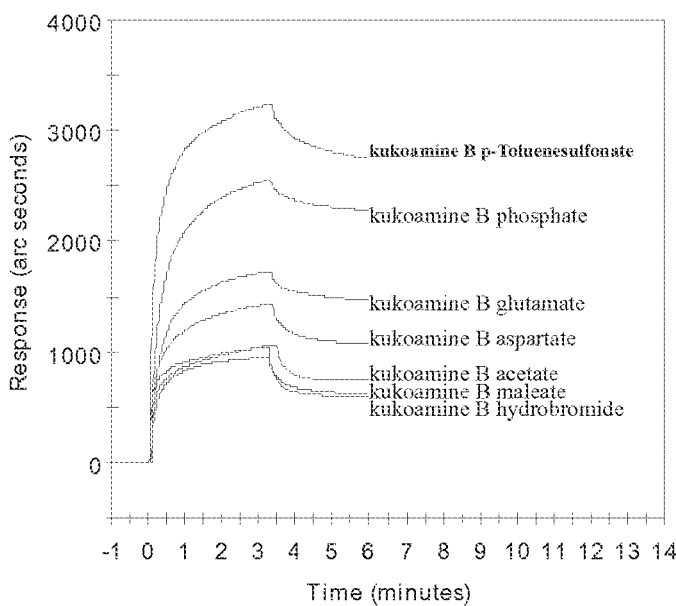

LPS and CpG DNA are key factors responsible for sepsis. Therefore, the antagonism of drugs on LPS and CpG DNA reflect their preventive and therapeutic effects on sepsis. The following examples are detailed description of embodiments of the present invention, in which, kukoamine B malate, kukoamine B succinate, kukoamine B lactate, kukoamine B tartrate, kukoamine B methanesulfonate, kukoamine B p-toluenesulfonate, kukoamine B glutamate, kukoamine B acetate, kukoamine B hydrochlorate, and kukoamine B sulfate, all of which are mature for pharmaceutical use, are particularly selected for illustration. However, it is to be understood that the disclosed embodiments are merely examples of the present invention, and are not intended to limit the disclosure in any way. It should be noted that any modifications and equivalent substitutions, which do not depart from the concept or scope of the present invention, are intended to be covered by the scope of appended claims.

All reagents used herein are analytical grade, unless expressly specified otherwise.

The following table is a list of abbreviations for reference.

| | |
|---|---|
| TLC | Thin-layer chromatography |
| DMF | N,N-dimethylformamide |
| MeOH | Methanol |
| HCl | Hydrochloric acid |
| $(Boc)_2O$ | Di-tert-butyl dicarbonate |
| DCM | Dichloromethane |
| EtOH | Ethanol |
| THF | Tetrahydrofuran |
| Cbz-Cl | Benzyl chloroformate |
| Raney Ni | Raney nickel |
| MPa | Megapascal |
| h | Hour |
| TFA | Trifluoroacetic acid |
| rt | Room temperature |
| Pd/C | Palladium-carbon catalyst |
| NMR | Nuclear magnetic resonance |
| PBS | Phosphate buffered solution |
| M | Moles per liter |
| Arc second | Arc second |

EXAMPLE 1

The Synthesis of Kukoamine B Malate 1.1 Methods: (1) 50 g of compound f1 is dissolved in 100 ml of hydrobromic acid solution (40% concentration), then heated to 140° C. to carry out the reaction, and the reaction is monitored via TLC. After the reaction is completed, the reaction solution is cooled down and then yellow crystals precipitate out. The yellow crystals are collected by suction filtration and washed with small quantity of petroleum ether, and then 40 g of yellow solid compounds f2 are obtained. Next, 40 g of compound f2 is dissolved in 120 ml of DMF, added with 116 g of potassium carbonate and 86 ml of benzyl chloride, and then heated to 80° C. to carry out the reaction, and the reaction is monitored via TLC. After the reaction is completed, the reaction solution is filtrated, extracted with ethyl acetate, washed sequentially with water and saturated salt water, and dried with anhydrous sodium sulfate, and then compound f3 is collected by suction filtration. Next, 14.4 g of sodium hydroxide is dissolved in 80 ml of water, added with 85 g of compound f3, then added with 80 ml of methanol, and heated to 90° C. to perform reflux reaction, and the reaction is monitored via TLC. After the reaction is completed, the reaction solution is dried by rotary evaporation, then poured into a beaker, added with concentrated hydrochloric acid to make it strongly acidic, and filtrated, and then the filter cake is collected and dried. 60 g of yellow compound f is obtained and the yield is 69%. The reaction equation is expressed as follows:

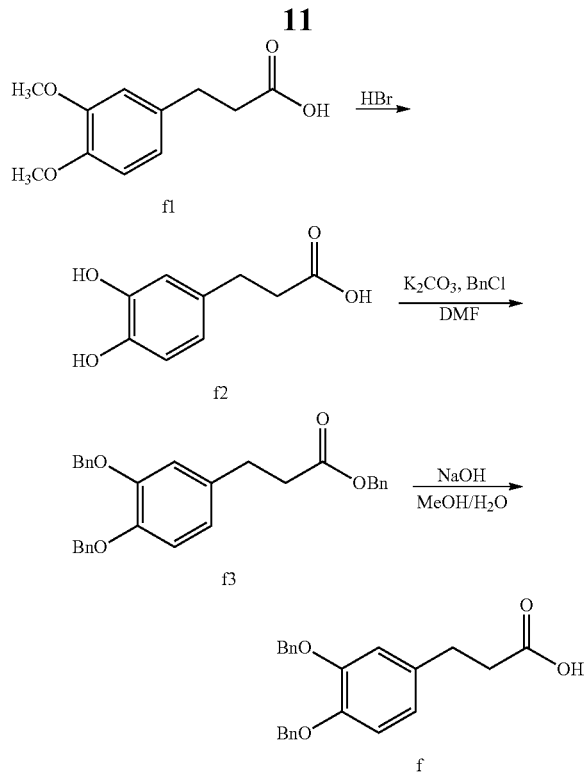

(2) 20 g of butanediamine (compound a) is added into a 500 ml round bottom flask, and added with 23 ml of 28% sodium hydroxide solution. After butanediamine has been completely dissolved, 200 ml of 12.5% ethanol solution of (Boc)$_2$O is dropwise added into the reaction solution at room temperature while agitating. The reaction is carried out under ceaseless agitation at room temperature and monitored via TLC. After the reaction is completed, the reaction solution is concentrated by rotary evaporation to remove ethanol, and extracted with DCM for several times until full extraction. The organic layers are merged, washed with saturated salt water, dried with anhydrous sodium sulfate, and treated by suction filtration after standing for some time. After concentration, 13.7 g of compound b, a colorless oil-like substance, is obtained, and the yield is 64%. The reaction equation is expressed as follows:

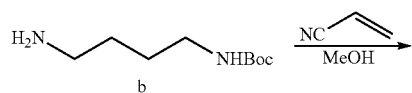

(3) 27 g of compound b is dissolved in 60 ml of methanol, and added with mixed solution containing 12 ml of acrylon and 20 ml of methanol dropwise at room temperature. The reaction is carried out under ceaseless agitation at room temperature and monitored via TLC. After the reaction is completed, the reaction solution is concentrated by rotary evaporation, and 31 g of compound c, a colorless oil-like substance, is obtained with the yield of 88.6%. The reaction equation is expressed as follows:

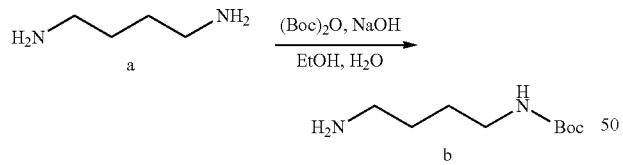

(4) 30 g of compound c is added into a 250 ml round bottom flask, added with 80 ml of THF and 26 ml of triethylamine, and added with the solution containing 21 ml of Cbz-Cl and 50 ml of THF dropwise at room temperature while agitating. The reaction is carried out under ceaseless agitation at room temperature and monitored via TLC. After the reaction is completed, the reaction solution is concentrated by rotary evaporation to remove organic solvents, extracted with ethyl acetate, washed sequentially with 1 mol/L HCl solution for 3 times, water, and saturated salt water, dried with anhydrous sodium sulfate, and then treated by suction filtration after standing for some time. After concentration, pale yellow oil-like substance is obtained, added with certain amount of petroleum ether, and stirred. Then, large amount of white solid precipitate out, which is treated by suction filtration, and washed with petroleum ether. 40 g of air dried compound d, a white solid, is obtained and the yield is 86%. The reaction equation is expressed as follows:

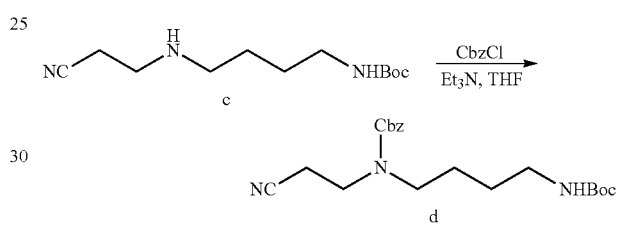

(5) 15 g of compound d is put into an autoclave, added with 150 ml of saturated methanol solution of ammonia to dissolve compound d, and then added with 4.5 g of Raney Ni after the solution goes clear. Aeration is applied to ensure the reaction system in hydrogen under 5-10 MPa. The reaction solution is heated to 50° C. to carry out the reaction while agitating, and the reaction is monitored via TLC. After the reaction is completed, the reaction solution is treated by suction filtration with diatomaceous earth. After concentration, 13.8 g of compound e, a blue oil-like substance, is obtained, and the yield is 92%. The reaction equation is expressed as follows:

(6) 13.1 g of compound f is dissolved in 40 ml of anhydrous DCM, added with 0.1 ml of DMF, and dropwise added with 3.9 ml of thionyl chloride under ceaseless agitation at room temperature. The reaction solution is heated to 45-65° C. to reflux for 5 h while agitating. Then, the reaction solution is concentrated by rotary evaporation to remove DCM, and compound f0 is obtained. The newly obtained compound f0 is added with anhydrous toluene, and treated by rotary evaporation to remove excess thionyl chloride. Besides, 13.8 g compound e is dissolved in 50 ml of anhydrous DCM, added with 12 ml of triethylamine, and dropwise added with the DCM solution of newly obtained compound f0 (10% of concentration) at 0° C. The reaction is monitored via TLC. After the reaction is completed, the reaction solution is treated by suction filtration, concentrated, extracted with diethyl ether, and washed sequentially with saturated potassium carbonate solution for three times, 1 mol/L HCL solution, water, and saturated salt water. Then, the extract is dried with anhydrous sodium sulfate, standing for some time, treated by suction filtration, and then dried by rotary evaporation. 23 g of compound g, a red oil-like substance, is obtained, and the yield is 88%. The reaction equation is expressed as follows:

(8) 18.1 g of compound h is dissolved in 40 ml of MeOH, added with 8 ml of triethylamine, heated to 60° C., and added with mixed solution containing 2.1 ml of acrylon and 15 ml of methanol dropwise while agitating. Then, the reaction solution is gradually cooled down to room temperature, ceaselessly agitated to carry out reaction, and the reaction is monitored via TLC. After the reaction is completed, the reaction solution is concentrated by rotary evaporation to remove organic solvent, and compound i is obtained. The reaction equation is expressed as follows:

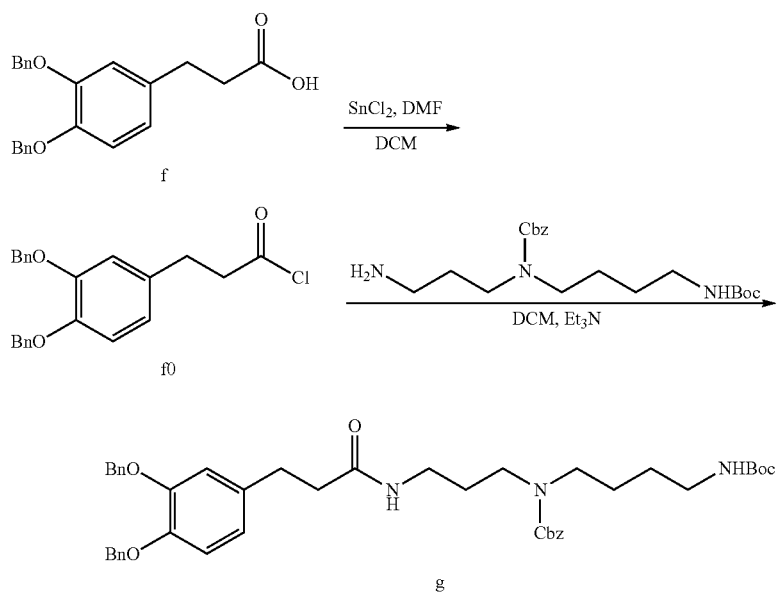 [SMILES: O=C(O)CCc1ccc(OCc2ccccc2)c(OCc2ccccc2)c1 ; O=C(Cl)CCc1ccc(OCc2ccccc2)c(OCc2ccccc2)c1 ; CC(C)(C)OC(=O)NCCCCN(CCCN)C(=O)OCc1ccccc1 ; CC(C)(C)OC(=O)NCCCCN(CCCNC(=O)CCc1ccc(OCc2ccccc2)c(OCc2ccccc2)c1)C(=O)OCc1ccccc1]

(7) 13 g of compound g is dissolved in 30 ml of DCM, added with 5 ml of TFA, and ceaselessly agitated at room temperature, and the reaction is monitored via TLC. After the reaction is completed, the reaction solution is concentrated by rotary evaporation to remove DCM, extracted with ethyl acetate, washed sequentially with water and saturated salt water, dried with anhydrous sodium sulfate, standing for some time, and then treated by suction filtration. After concentration, 11 g of compound h, a red oil-like substance, is obtained, and the yield is 85%. The reaction equation is expressed as follows:

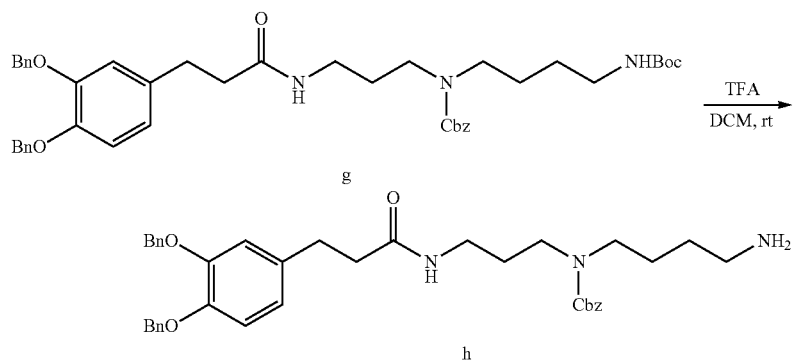

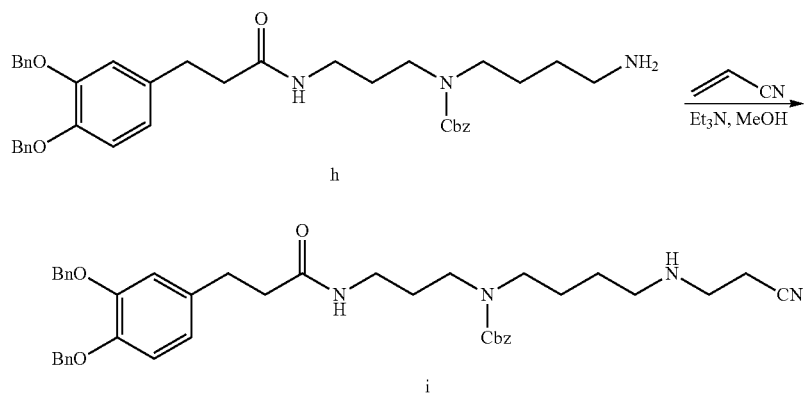

(9) 10.5 g of compound f is put into a 100 ml round bottom flask, added with 35 ml of anhydrous DCM, added with two drops (0.1 ml) of DMF, dropwise added with 2.6 ml of thionyl chloride, and heated to 45-65° C. to reflux for 4 h. Then, the reaction solution is concentrated by rotary evaporation to remove DCM, and compound f0 is obtained. The newly obtained compound f0 is added with anhydrous toluene, and treated by rotary evaporation to remove excess thionyl chloride. Besides, 19.6 g of compound i is dissolved in 50 ml of anhydrous DCM, added with 12 ml of triethylamine, and dropwise added with the DCM solution of newly obtained compound f0 (10% of concentration) at 0° C., and the reaction is monitored via TLC. After the reaction is completed, the reaction solution is treated by suction filtration, concentrated, extracted with ethyl acetate, washed sequentially with saturated potassium carbonate solution for three times, 1 mol/L HCl solution, water, and saturated salt water, dried with anhydrous sodium sulfate, standing for some time, treated by suction filtration, dried by rotary evaporation to obtain a red oil-like substance. The red oil-like substance is isolated by silica gel column chromatography for silica gel of 200-300 mesh as stationary phase and ethyl acetate-petroleum ether (2:1) as mobile phase. All the eluant is collected and concentrated up to dryness. 21 g of compound j is obtained, and the yield is 79%. The reaction equation is expressed as follows:

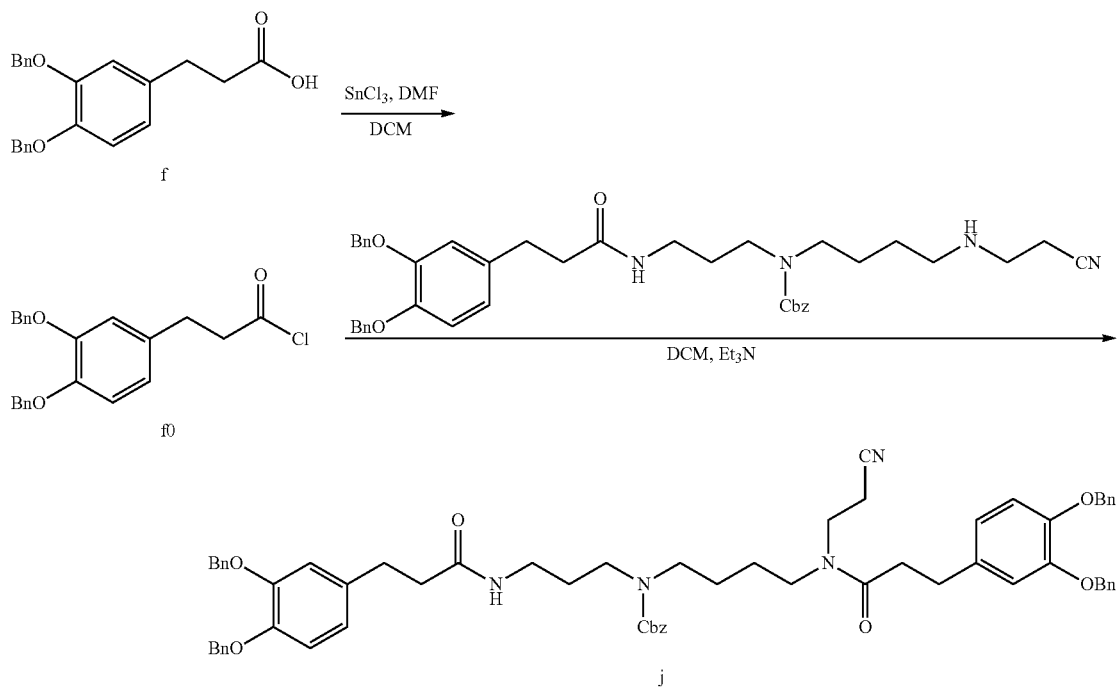

(10) 20 g of compound j is put into an autoclave and added with 400 ml of mixed solution containing saturated methanol solution of ammonia and THF with the volume ratio of 3:1, and aeration is applied to ensure the reaction system in hydrogen under 1-2 MPa. The reaction is carry out under ceaseless agitation at 50° C. and monitored via TLC. After the reaction is completed, the reaction solution is treated by suction filtration and concentrated, and 18.6 g of compound k, a blue oil-like substance, is obtained. The yield is 93%. The reaction equation is expressed as follows:

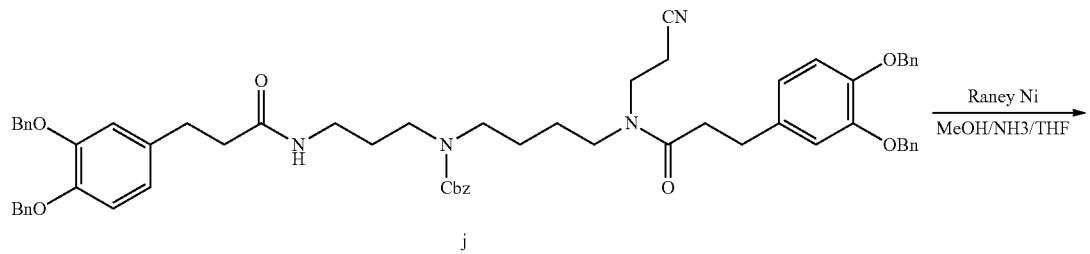

j

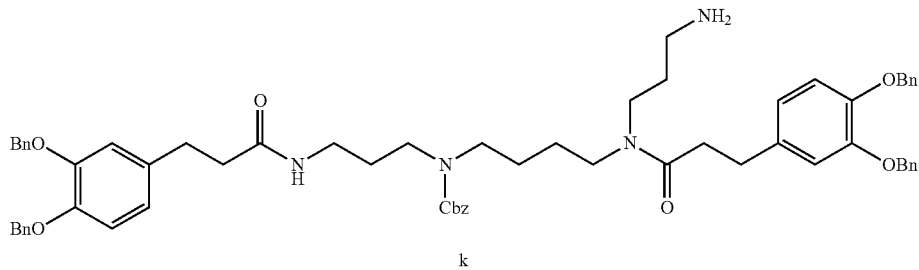

k

(11) 1 g of compound k and 0.8 g of malic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and dark green semisolid is obtained. The dark green semisolid is added with 30 ml of ethanol, treated by ultrasonic vibration, standing for some time to precipitate, and then the supernatant is discarded; this process is repeated for several times. Finally, 407 mg of dark green solid powder is obtained by suction filtration. The reaction equation is expressed as follows:

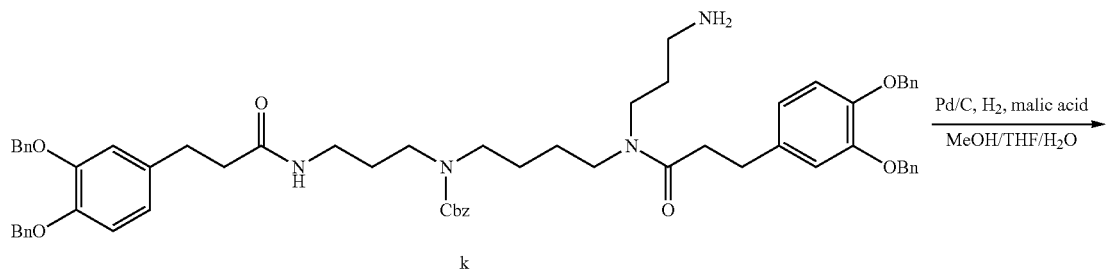

k

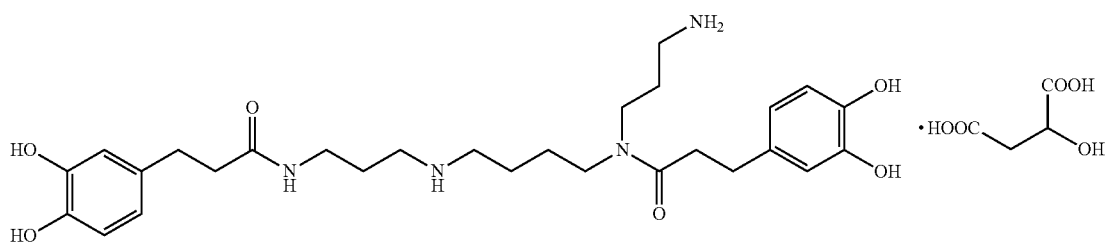

1.2 Results: 407 mg of dark green solid powder is obtained. UV spectrum: $\lambda_{max}$ nm=280 (methanol); mass spectrometry: [M+H]$^+$ m/z 531.36; H-nuclear magnetic resonance ($^1$H-NMR) (400 MHz, D$_2$O): δ (ppm) 6.88-6.73 (m, 6H), 4.41 (s, 1H), 3.43-3.23 (m, 6H), 2.86-2.59 (m, 16H), 1.87-1.41 (m, 8H). The dark green solid powder is identified as kukoamine B malate, the chemical structure of which is shown as follows:

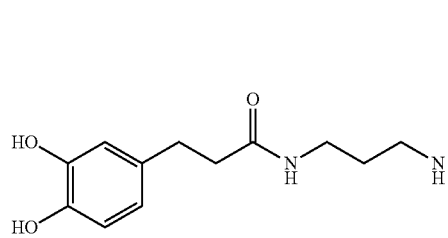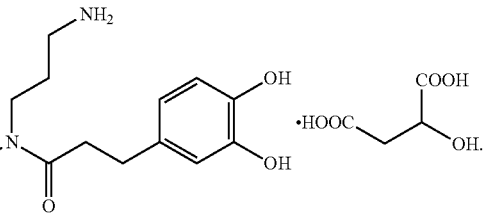

EXAMPLE 2

The Synthesis of Kukoamine B Succinate 2.1 Methods: Steps (1) through (10) are identical to the steps (1) through (10) in embodiment 1, respectively;

(11) 1 g of compound k and 0.71 g of succinic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and dark green semisolid is obtained. The dark green semisolid is added with 30 ml of ethanol, treated by ultrasonic vibration, standing for some time to precipitate, and then the supernatant is discarded; this process is repeated for several times. Finally, 365 mg of dark green solid powder is obtained by suction filtration. The reaction equation is expressed as follows:

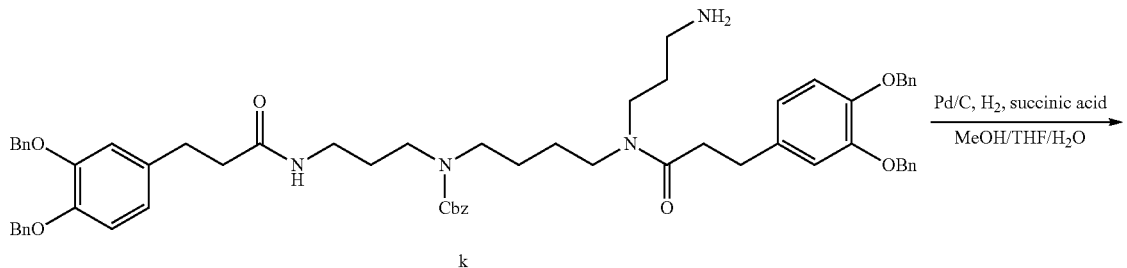

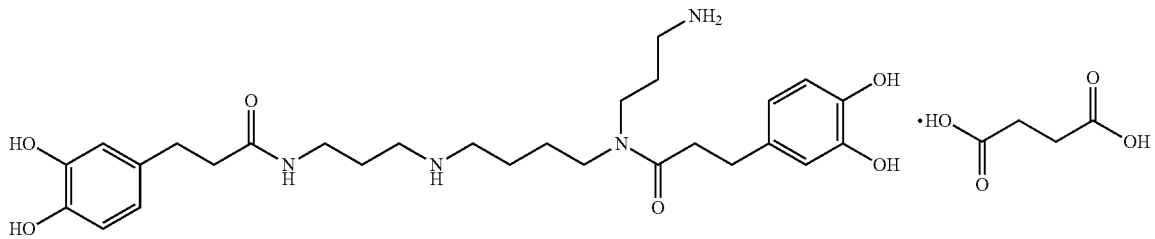

2.2 Results: 365 mg of dark green powdered solid is obtained. UV spectrum: $\lambda_{max}$ nm=280 (methanol); mass spectrometry: $[M+H]^+$ m/z 531.36. The dark green powdered solid is identified as kukoamine B succinate, the chemical structure of which is shown as follows:

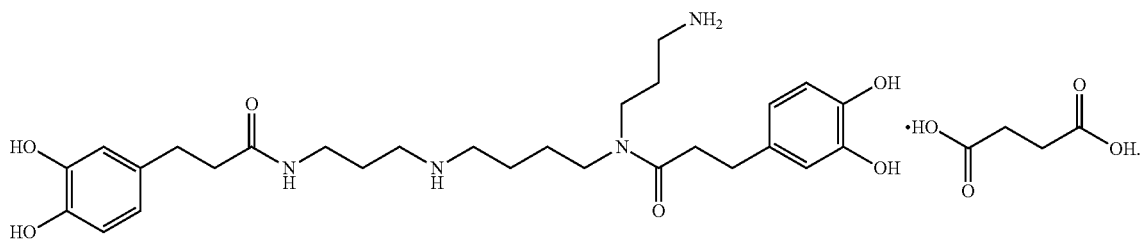

EXAMPLE 3

The Synthesis of Kukoamine B Lactate 3.1 Methods: Steps (1) through (10) are identical to the steps (1) through (10) in embodiment 1, respectively;

(11) 1 g of compound k and 0.5 ml of lactic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and yellow semisolid is obtained. The yellow semisolid is added with 30 ml of ethanol, treated by ultrasonic vibration, standing for some time to precipitate, and then the supernatant is discarded; this process is repeated for several times. Finally, 340 mg of yellow solid powder is obtained by suction filtration. The reaction equation is expressed as follows:

EXAMPLE 4

The Synthesis of Kukoamine B tartrate 4.1 Methods: Steps (1) through (10) are identical to the steps (1) through (10) in embodiment 1, respectively;

(11) 1 g of compound k and 0.9 g of tartaric acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and yellow semisolid is obtained. The yellow semisolid is added with 30 ml of ethanol, treated by ultrasonic vibration, standing for some time to precipitate, and then the supernatant is discarded; this process is repeated for several times. Finally, 383 mg of yellow solid powder is obtained by suction filtration. The reaction equation is expressed as follows:

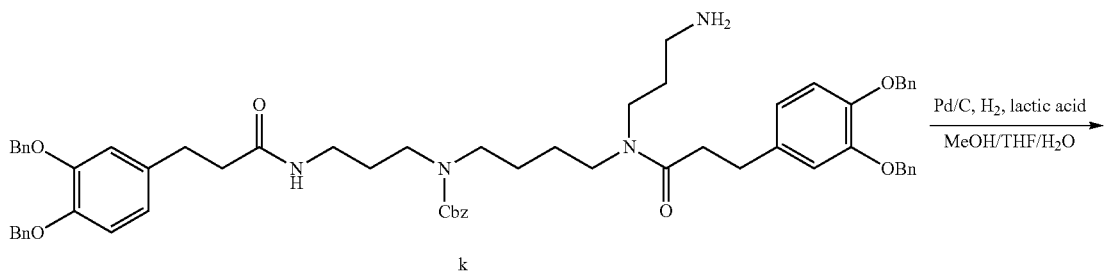

3.2 Results: 340 mg of yellow powdered solid is obtained. UV spectrum: $\lambda_{max}$ nm=280 (methanol); mass spectrometry: $[M+H]^+$ m/z 531.36. The yellow powdered solid is identified as kukoamine B lactate, the chemical structure of which is shown as follows:

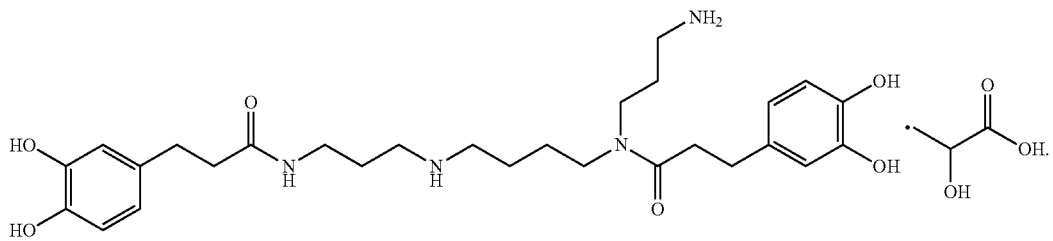

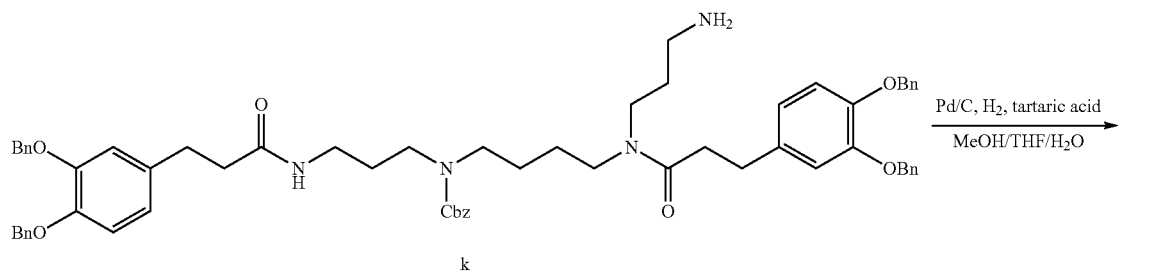

k

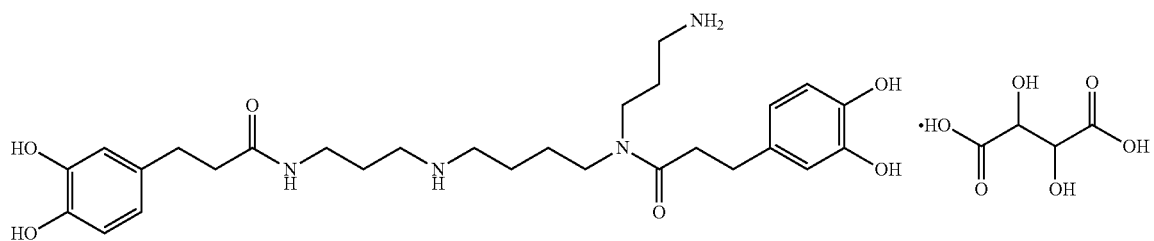

4.2 Results: 383 mg of yellow powdered solid is obtained. UV spectrum: $\lambda_{max}$ nm=280 (methanol); mass spectrometry: [M+H]$^+$ m/z 531.36. The yellow powdered solid is identified as kukoamine B tartrate, the chemical structure of which is shown as follows:

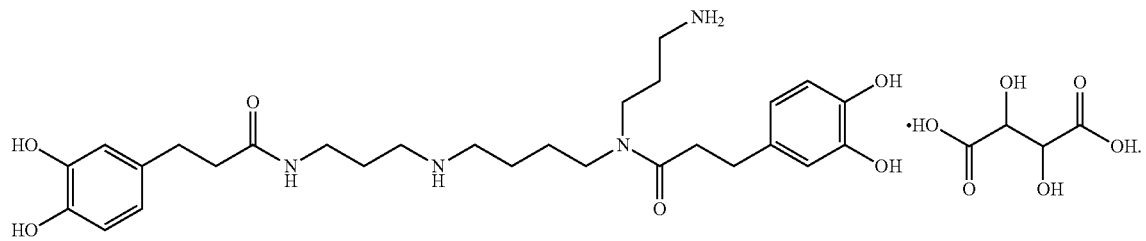

EXAMPLE 5

The Synthesis of Kukoamine B methanesulfonate 5.1 Methods: Steps (1) through (10) are identical to the steps (1) through (10) in embodiment 1, respectively;

(11) 1.0 g of compound k and 0.58 g of methanesulfonic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 355 mg of pale yellow solid powder is obtained by suction filtration. The reaction equation is expressed as follows:

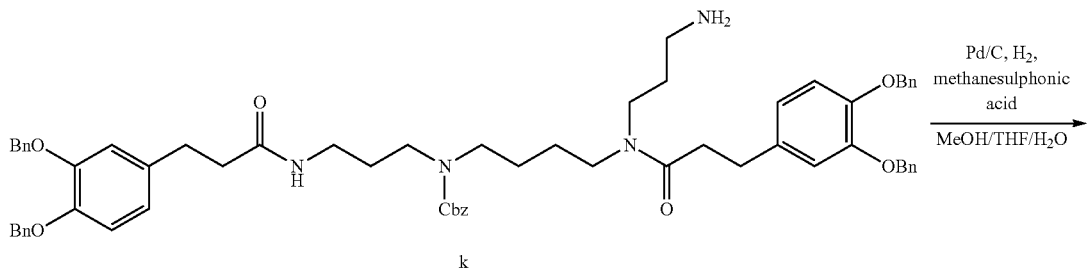

k

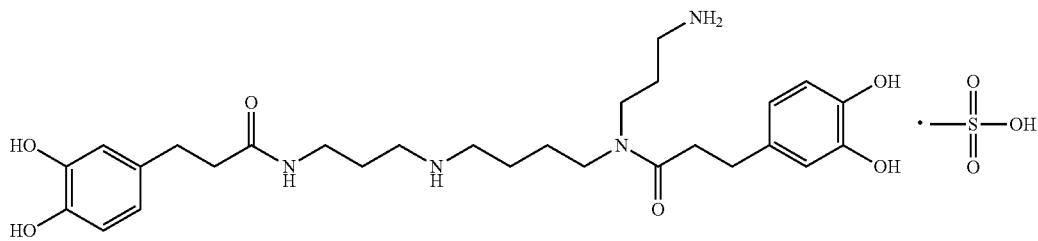

5.2 Results: 355 mg of pale yellow powdered solid is obtained. UV spectrum: $\lambda_{max}$ nm=280 (methanol); mass spectrometry: [M+H]$^+$ m/z 531.36. The pale yellow powdered solid is identified as kukoamine B methanesulfonate, the chemical structure of which is shown as follows:

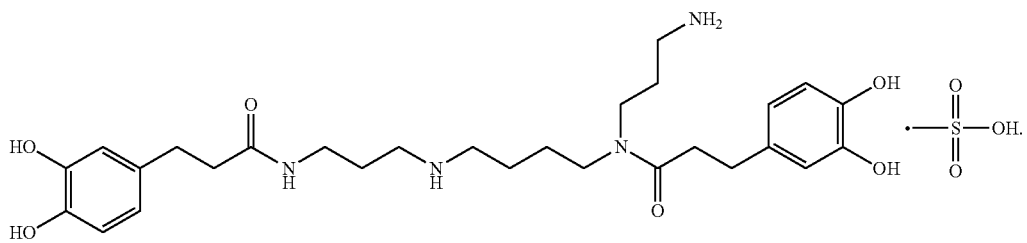

EXAMPLE 6

The Synthesis of Kukoamine B p-toluenesulfonate 6.1 Methods: Steps (1) through (10) are identical to the steps (1) through (10) in embodiment 1, respectively;

(11) 1 g of compound k and 1 g of p-toluenesulfonic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 396 mg of pale yellow solid powder is obtained by suction filtration. The reaction equation is expressed as follows:

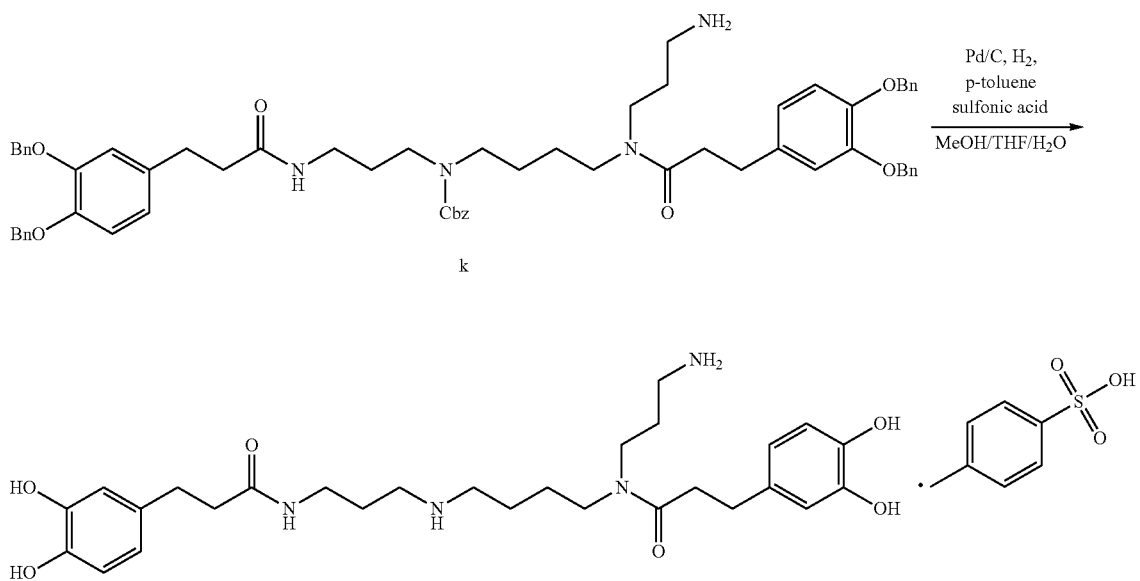

6.2 Results: 396 mg of pale yellow powdered solid is obtained. UV spectrum: $\lambda_{max}$ nm=280 (methanol); mass spectrometry: [M+H]$^+$ m/z 531.36. The pale yellow powdered solid is identified as kukoamine B p-toluenesulfonate, the chemical structure of which is shown as follows:

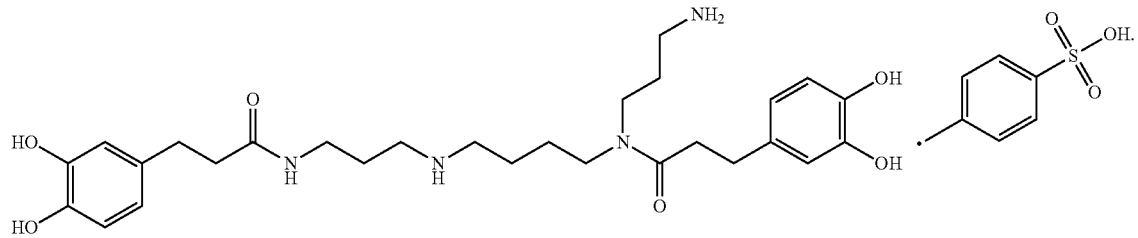

EXAMPLE 7

The Synthesis of Kukoamine B Glutamate 7.1 Methods: Steps (1) through (10) are identical to the steps (1) through (10) in embodiment 1, respectively;

(11) 1.0 g of compound k and 0.88 g of glutamic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 380 mg of pale yellow solid powder is obtained by suction filtration. The reaction equation is expressed as follows:

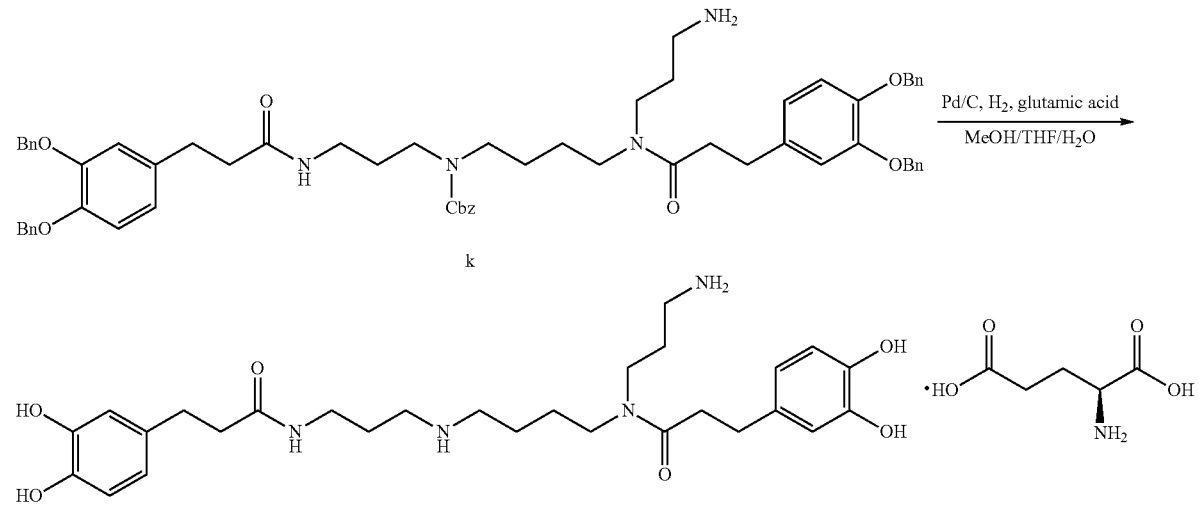

7.2 Results: 380 mg of pale yellow powdered solid is obtained. UV spectrum: $\lambda_{max}$ nm =280 (methanol); mass spectrometry: [M+H]$^+$ m/z 531.36. The pale yellow powdered solid is identified as kukoamine B glutamate, the chemical structure of which is shown as follows:

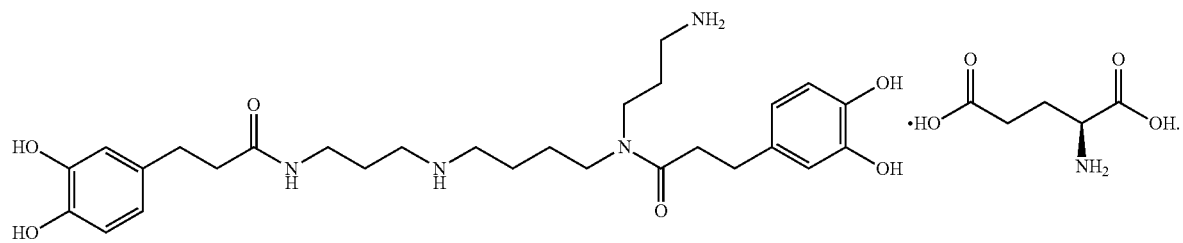

EXAMPLE 8

The Synthesis of Kukoamine B Acetate 8.1 Methods: Steps (1) through (10) are identical to the steps (1) through (10) in embodiment 1, respectively;

(11) 1.0 g of compound k and 0.4 ml of acetic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 330 mg of pale yellow solid powder is obtained by suction filtration. The reaction equation is expressed as follows:

EXAMPLE 9

The Synthesis of Kukoamine B Hydrochlorate 9.1 Methods: Steps (1) through (10) are identical to the steps (1) through (10) in embodiment 1, respectively;

(11) 1 g of compound k and 0.64 ml of hydrochloric acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and yellow semisolid is obtained. The yellow semisolid is added with 30 ml of ethanol, treated by ultrasonic vibration, standing for some time to precipitate, and then the supernatant is discarded; this process is repeated for several times. Finally, 320 mg of yellow solid powder is obtained by suction filtration. The reaction equation is expressed as follows:

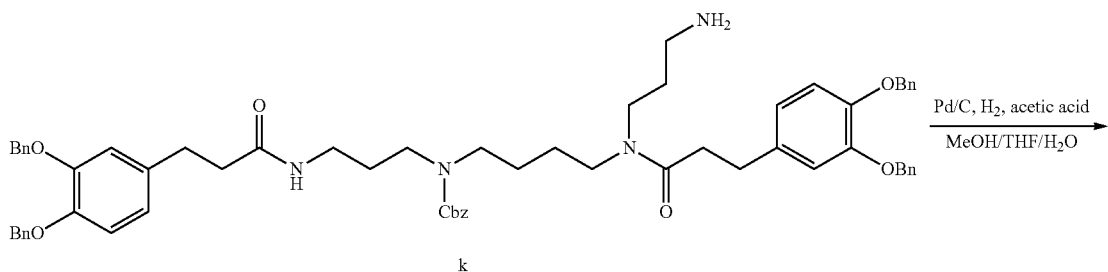

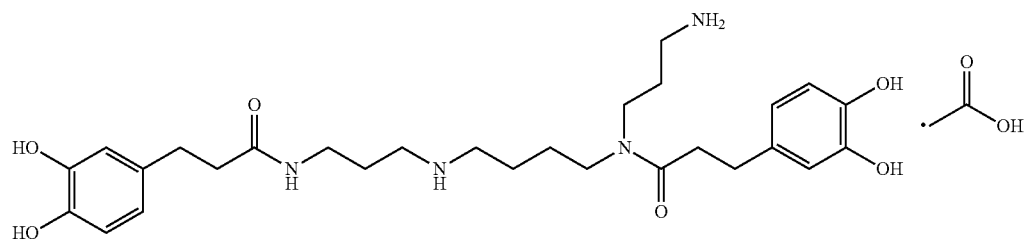

8.2 Results: 330 mg of pale yellow powdered solid is obtained. UV spectrum: $\lambda_{max}$ nm=280 (methanol); mass spectrometry: [M+H]$^+$ m/z 531.36. The pale yellow powdered solid is identified as kukoamine B acetate, the chemical structure of which is shown as follows:

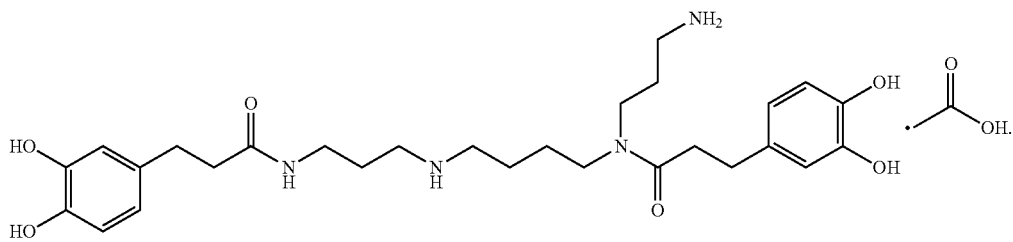

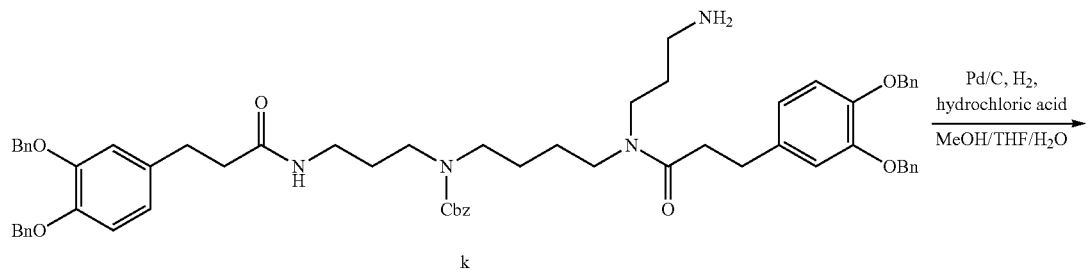

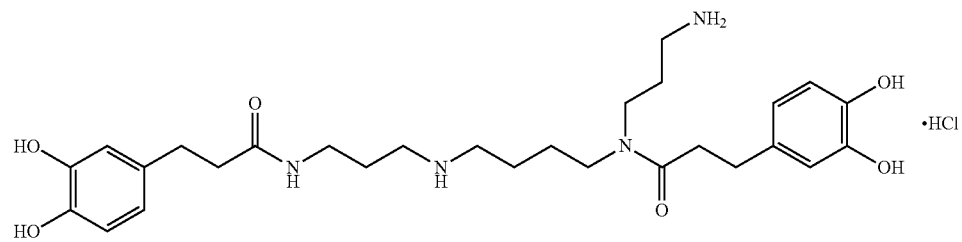

9.2 Results: 320 mg of yellow powdered solid is obtained. UV spectrum: $\lambda_{max}$ nm=280 (methanol); mass spectrometry: $[M+H]^+$ m/z 531.36. The yellow powdered solid is identified as kukoamine B hydrochlorate, the chemical structure of which is shown as follows:

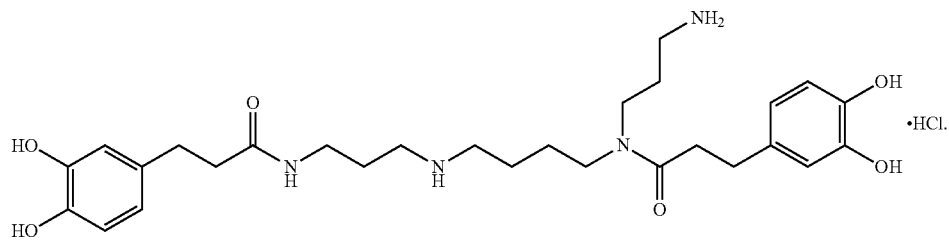

EXAMPLE 10

The Synthesis of Kukoamine B Sulfate 10.1 Methods: Steps (1) through (10) are identical to the steps (1) through (10) in embodiment 1, respectively;

(11) 1.0 g of compound k and 0.4 ml of sulfuric acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 355 mg of pale yellow solid powder is obtained by suction filtration. The reaction equation is expressed as follows:

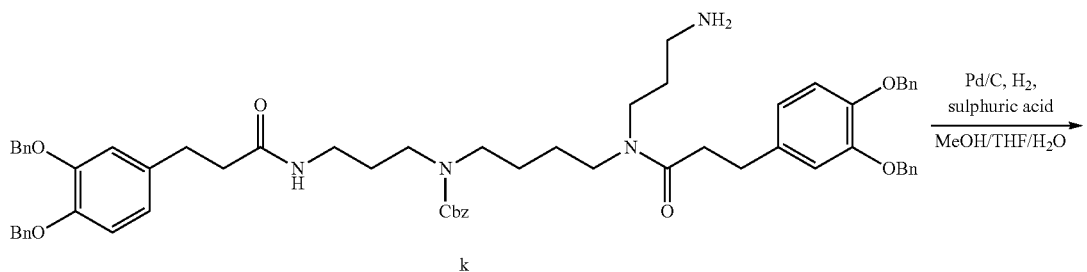

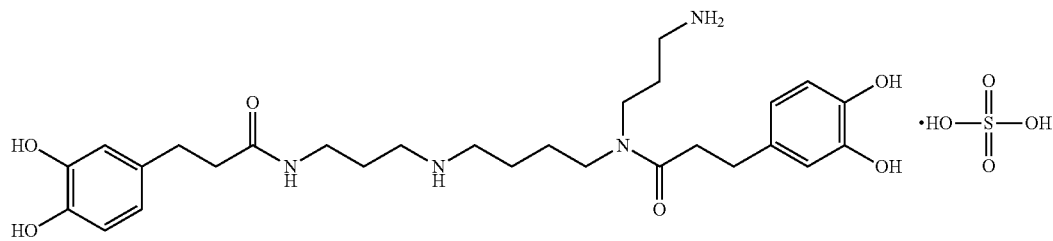

10.2 Results: 355 mg of pale yellow powdered solid is obtained. UV spectrum: $\lambda_{max}$ nm=280 (methanol); mass spectrometry: [M+H]$^+$ m/z 531.36. The pale yellow powdered solid is identified as kukoamine B sulfate, the chemical structure of which is shown as follows:

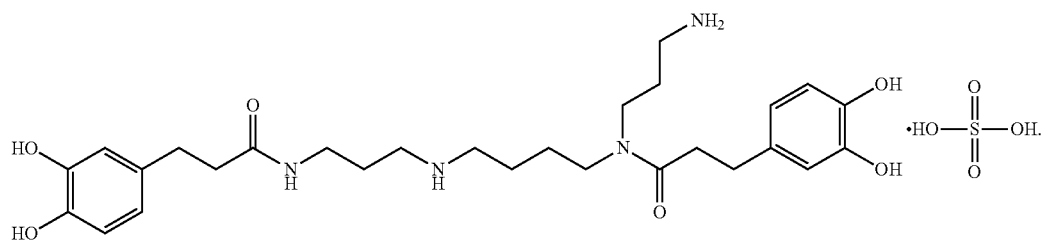

EXAMPLE 11

The Synthesis of Kukoamine B Maleate 11.1 Methods: Steps (1) through (10) are identical to the steps (1) through (10) in embodiment 1, respectively;

(11) 1.0 g of compound k and 0.7 g of maleic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and yellow semisolid is obtained. The yellow semisolid is added with 30 ml of ethanol, treated by ultrasonic vibration, standing for some time to precipitate, and then the supernatant is discarded; this process is repeated for several times. Finally, 365 mg of yellow solid powder is obtained by suction filtration. The reaction equation is expressed as follows:

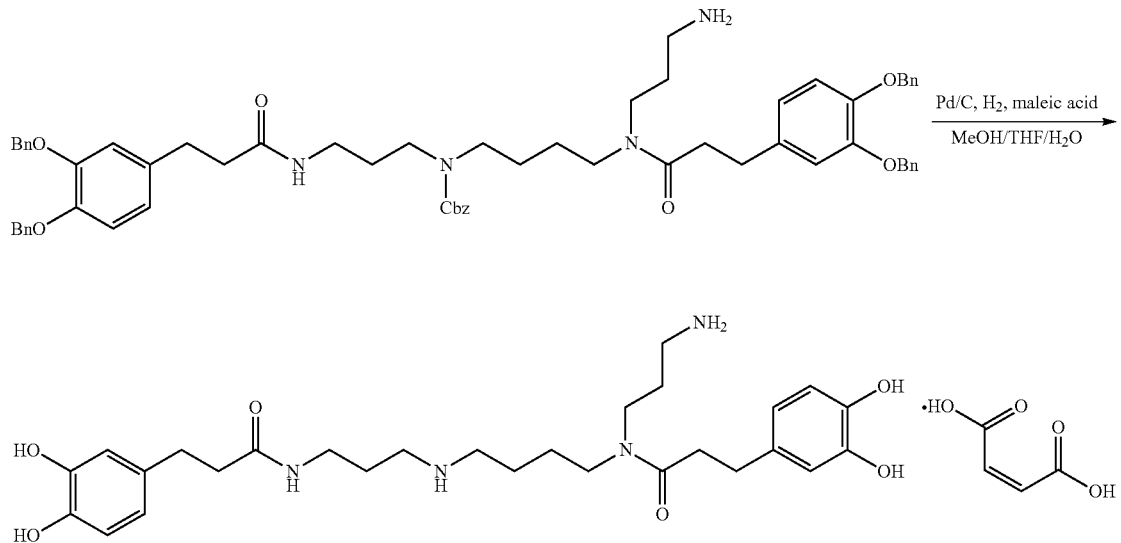

11.2 Results: 365 mg of yellow powdered solid is obtained. UV spectrum: $\lambda_{max}$ nm=280 (methanol); mass spectrometry: [M+H]$^+$ m/z 531.36. The yellow powdered solid is identified as kukoamine B maleate, the chemical structure of which is shown as follows:

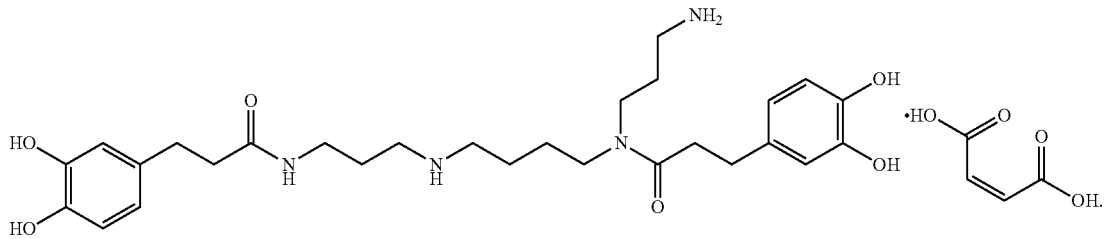

EXAMPLE 12

The Synthesis of Kukoamine B Aspartate 12.1 Methods: Steps (1) through (10) are identical to the steps (1) through (10) in embodiment 1, respectively;

(11) 1.0 g of compound k and 0.8 g of aspartic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 374 mg of pale yellow solid powder is obtained by suction filtration. The reaction equation is expressed as follows:

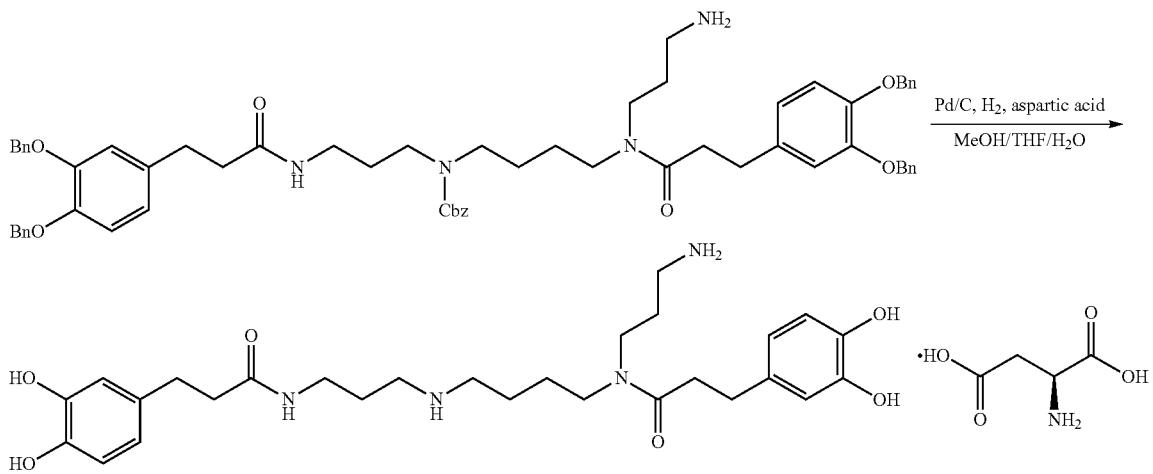

12.2 Results: 374 mg of pale yellow powdered solid is obtained. UV spectrum: $\lambda_{max}$ nm=280 (methanol); mass spectrometry: [M+H]$^+$ m/z 531.36. The pale yellow powdered solid is identified as kukoamine B aspartate, the chemical structure of which is shown as follows:

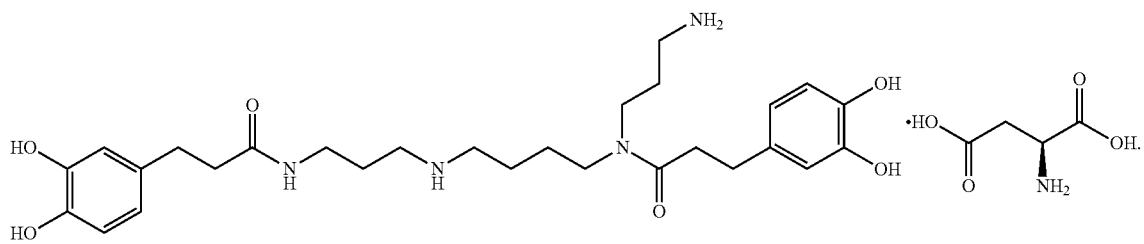

EXAMPLE 13

The Synthesis of Kukoamine B Hydrobromide 13.1 Methods: Steps (1) through (10) are identical to the steps (1) through (10) in embodiment 1, respectively;

(11) 1.0 g of compound k and 0.5 ml of hydrobromic acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 345 mg of pale yellow solid powder is obtained by suction filtration. The reaction equation is expressed as follows:

EXAMPLE 14

The Synthesis of Kukoamine B Phosphate 14.1 Methods: Steps (1) through (10) are identical to the steps (1) through (10) in embodiment 1, respectively;

(11) 1.0 g of compound k and 0.4 ml of phosphoric acid are put into an autoclave, added with 30 ml of mixed solution containing MeOH, THF and water with the volume ratio of 3:1:1, and then added with 0.2 g of Pd/C catalyst after the solution goes clear. Aeration is applied to ensure the reaction system in hydrogen under 10 MPa. The reaction solution is heated to 45° C. to carry out the reaction, and the reaction is monitored via TLC. After the reaction is completed, the reaction solution is treated by suction filtration and concentrated up to dryness, and pale yellow semisolid is obtained. The pale yellow semisolid is added with 30 ml of ethanol, treated by ultrasonic vibration, standing for some time to precipitate, and then the supernatant is discarded; this process is repeated for several times. Finally, 354 mg of pale yellow solid powder is obtained by suction filtration. The reaction equation is expressed as follows:

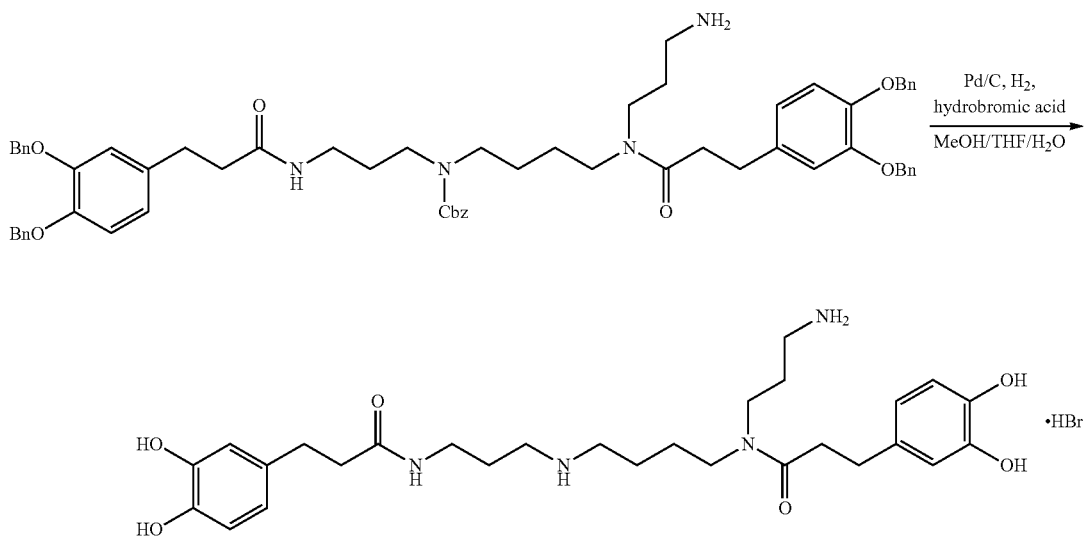

13.2 Results: 345 mg of pale yellow powdered solid is obtained. UV spectrum: $\lambda_{max}$ nm=280 (methanol); mass spectrometry: $[M+H]^+$ m/z 531.36. The pale yellow powdered solid is identified as kukoamine B hydrobromide, the chemical structure of which is shown as follows:

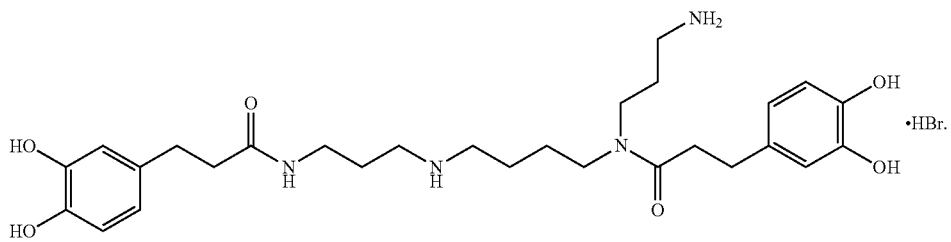

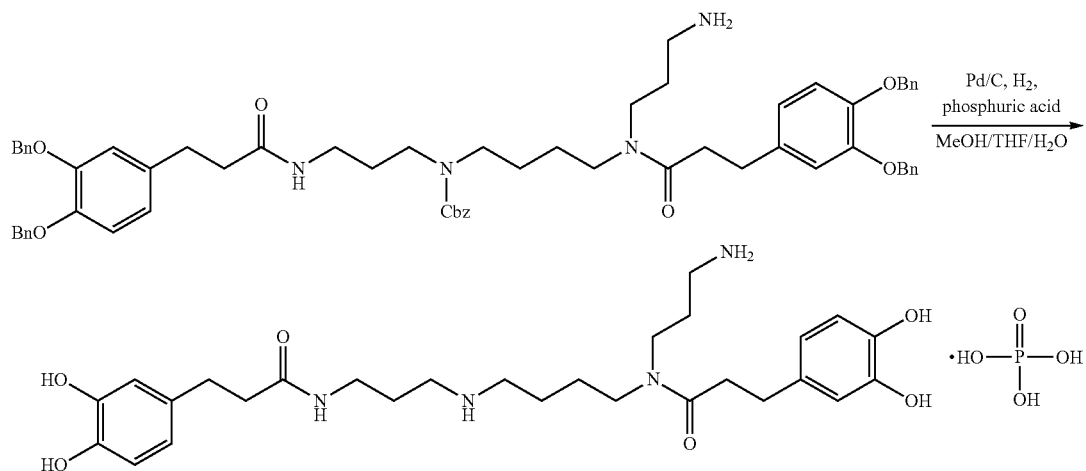

14.2 Results: 354 mg of pale yellow powdered solid is obtained. UV spectrum: $\lambda_{max}$ nm=280 (methanol); mass spectrometry: $[M+H]^+$ m/z 531.36. The pale yellow powdered solid is identified as kukoamine B phosphate, the chemical structure of which is shown as follows:

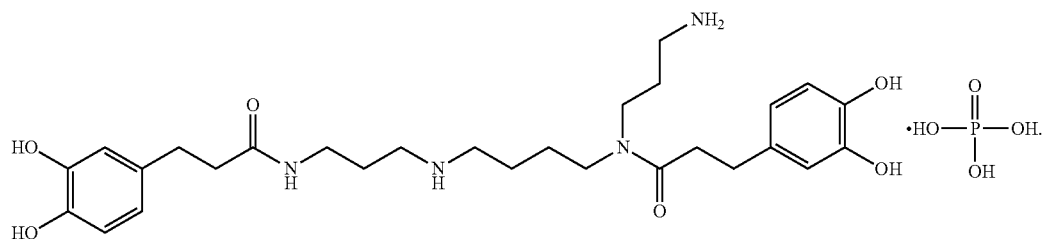

EXAMPLE 15

The Affinity Assay of Salts of Kukoamine B with Lipid A 15.1 Methods: The affinity assay is carried out according to the methods disclosed in the Chinese patent titled "Use of an active ingredient or active substance selected and isolated from traditional Chinese herbs in the preparation of drugs for treating sepsis" (Chinese patent Number ZL 200510070677.3) granted to the applicant, which mainly comprises the following steps:

(1) Lipid A is immobilized on the reacting surfaces of non-derivative cuvettes according to the instructions of immobilization of lipid in the manufacturer's instructions of IAsys plus Affinity Sensor. Wherein, the end of hydrophobic side chain of lipid A was immobilized on cuvette, and the hydrophilic end is floating outside, which act as target site of binding reaction;

(2) 1 mg of each of the salts, including kukoamine B hydrochlorate, kukoamine B hydrobromide, kukoamine B sulfate, kukoamine B phosphate, kukoamine B acetate, kukoamine B maleate, kukoamine B succinate, kukoamine B malate, kukoamine B lactate, kukoamine B tartrate, kukoamine B methanesulfonate, kukoamine B p-toluenesulfonate, kukoamine B glutamate, and kukoamine B aspartate, is fully dissolved by 1 ml of PBS solution (0.01 M, pH 7.4), respectively;

(3) 5 μl of each of the solution obtained in step (2) is added into the affinity sensor's cuvettes (containing 45 μl of PBS solution) previously immobilized with lipid A to carry out the reaction, respectively;

(4) The binding reaction is carried out for 3 min, and the binding curves are recorded;

(5) Each of the cuvettes is washed with 50 μl of PBS solution for 3 times, and dissociation curves are recorded;

(6) Each of the cuvettes is washed with 0.1 M HCl solution for 3 times, and the regeneration curves are recorded.

15.2 Results: Each of the salts of kukoamine B mentioned above can bind with lipid A, and the binding curves are shown in FIG. 1. FIG. 1 shows the binding reaction of salts of kukoamine B with lipid A, wherein: FIG. 1A shows the results of kukoamine B malate, kukoamine B succinate, kukoamine B lactate, kukoamine B tartrate, kukoamine B methanesulfonate, kukoamine B hydrochlorate, and kukoamine B sulfate; and FIG. 1B shows the results of kukoamine B p-toluenesulfonate, kukoamine B glutamate, kukoamine B acetate, kukoamine B maleate, kukoamine B aspartate, kukoamine B hydrobromide, and kukoamine B phosphate.

EXAMPLE 16

Figure 2:
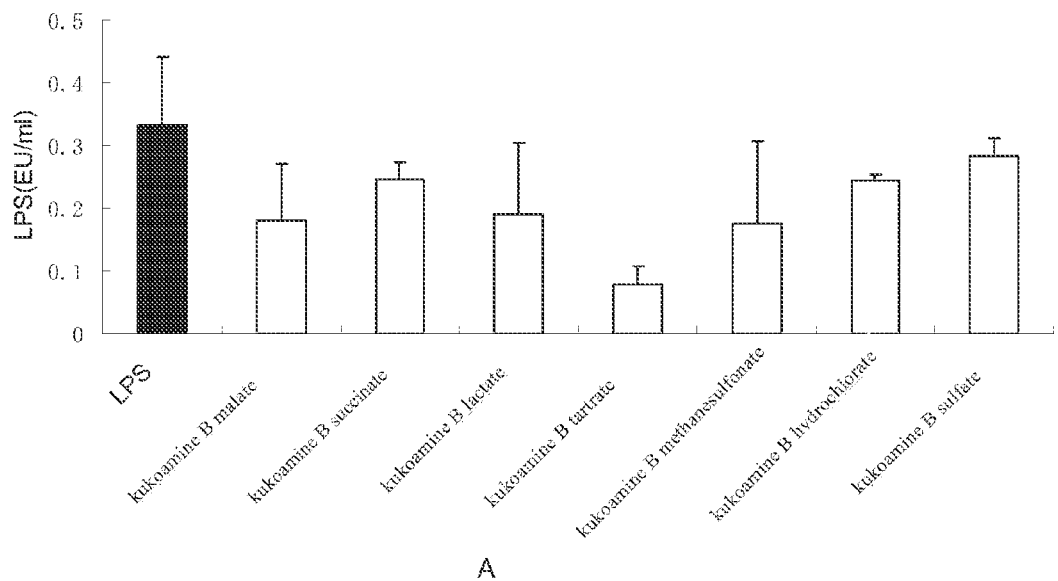
FIG. 2 shows the neutralization of salts of kukoamine B with LPS in vitro.
Figure 2:
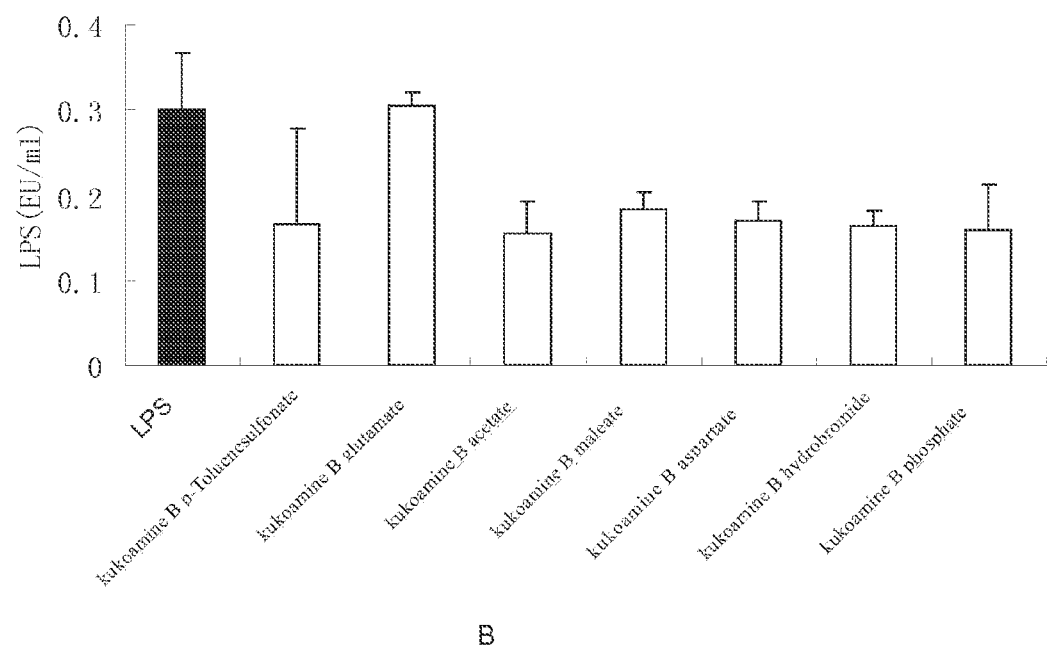

The Neutralizing Test of Salts of Kukoamine B on LPS in Vitro 16.1 Methods: The neutralizing test is carried out according to the manufacturer's instructions of 32 Well Kinetic Tube Reader (ATi321-06) endotoxin detector, which mainly comprises the following steps:

(1) Each of the salts, including kukoamine B hydrochlorate, kukoamine B hydrobromide, kukoamine B sulfate, kukoamine B phosphate, kukoamine B acetate, kukoamine B maleate, kukoamine B succinate, kukoamine B malate, kukoamine B lactate, kukoamine B tartrate, kukoamine B methanesulfonate, kukoamine B p-toluenesulfonate, kukoamine B glutamate, and kukoamine B aspartate, is prepared into 20 μM solution with nonpyrogenic water, respectively;

(2) 100 μl of each of the solution obtained in step (1) is separately mixed with equal volume of LPS solution (0.25 ng/ml). At the same time, the control group is established, which is a mixed solution containing 100 μl of nonpyrogenic water and equal volume of LPS solution (0.25 ng/ml). The LPS group and control group are incubated at 37° C. for 30 min. Then, 100 μl of the reaction solutions of LPS group and control group are separately added into a detector tube containing 100 μl of TAL reagents, and LPS value of each group are detected by kinetic turbidimetric limulus test according to the manufacturer's instructions of 32 Well Kinetic Tube Reader (ATi321-06) Bacterial Endotoxin Detection system. The test of each concentration is repeated three times;

16.2 Results: Each of the salts of kukoamine B can neutralize LPS in vitro, and the results are shown in FIG. 2, wherein: FIG. 2A shows the results of kukoamine B malate, kukoamine B succinate, kukoamine B lactate, kukoamine B tartrate, kukoamine B methanesulfonate, kukoamine B hydrochlorate, and kukoamine B sulfate; and FIG. 2B shows the results of kukoamine B p-toluenesulfonate, kukoamine B glutamate, kukoamine B acetate, kukoamine B maleate, kukoamine B aspartate, kukoamine B hydrobromide, and kukoamine B phosphate.

EXAMPLE 17

The Test about the Inhibition of Salts of Kukoamine B on the Release of Inflammatory Mediators in RAW264.7 Cells Induced by LPS 17.1 Methods: RAW264.7 cells are diluted to $1 \times 10^6$/ml in DMEM culture medium, added into a 96-well cell culture plate (200 μl per well), and incubated at 37° C. in a 5% $CO_2$ humidified incubator for 4 h, and then the supernatant is replaced with 200 μl of serum-free DMEM culture medium after cells attachment. Next, each well is added with LPS (final concentration of 100 ng/ml), and then added with one of the salts of kukoamine B (including kukoamine B malate, kukoamine B succinate, kukoamine B lactate, kukoamine B tartrate, kukoamine B methanesulfonate, kukoamine B p-toluenesulfonate, kukoamine B glutamate, kukoamine B acetate, kukoamine B hydrochlorate, and kukoamine B sulfate) to obtain the final concentration of 0, 50, 100, and 200 μM, respectively. The control group contains no LPS. Then, the incubation goes on for 4 h. The supernatant is collected to measure the concentration of TNF-α according to the manufacturer's instructions of ELISA kit.

Figure 3:
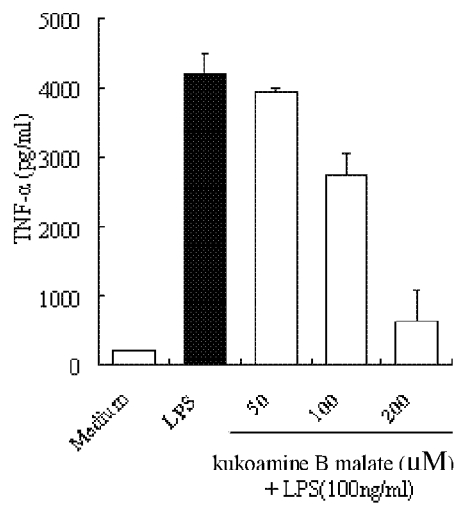
FIG. 3 shows the inhibition of salts of kukoamine B on the release of inflammatory mediators in RAW264.7 cells induced by LPS.
Figure 3:
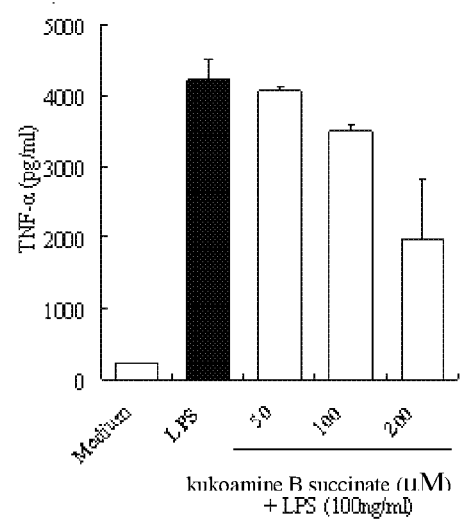
Figure 3:
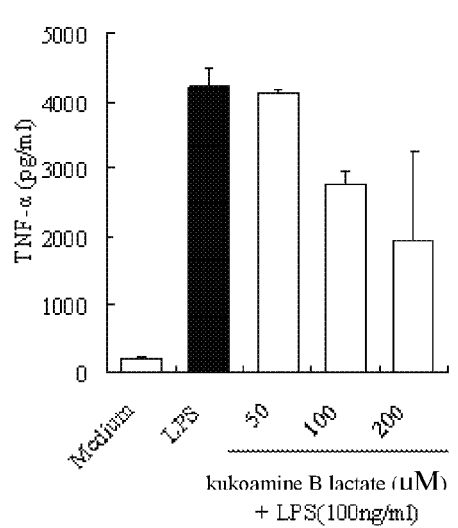
Figure 3:
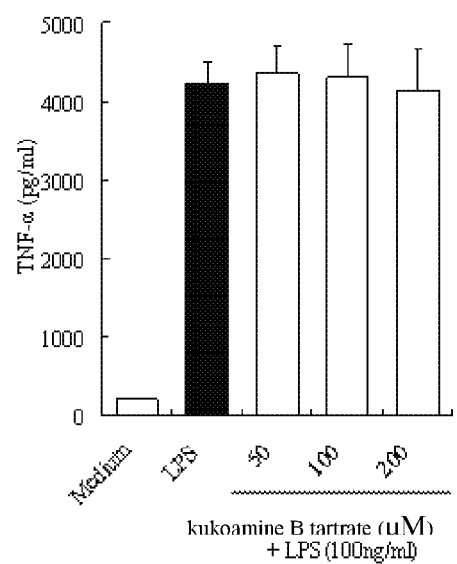
Figure 3:
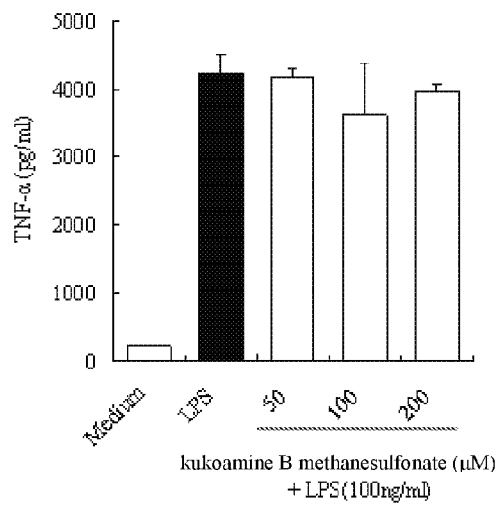
Figure 3:
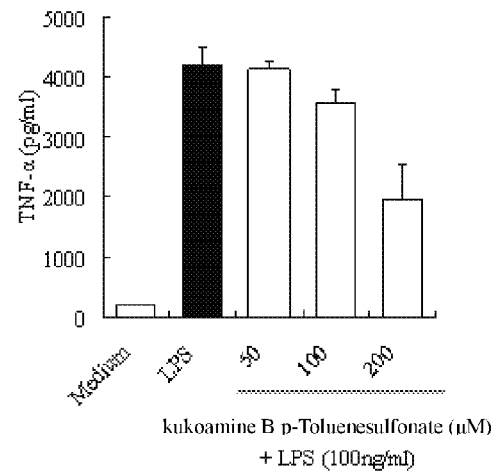
Figure 3:
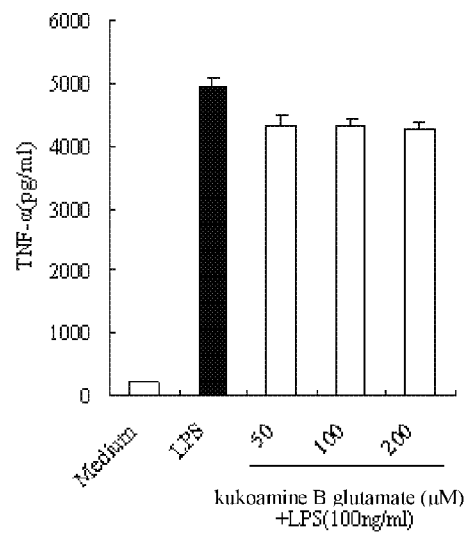
Figure 3:
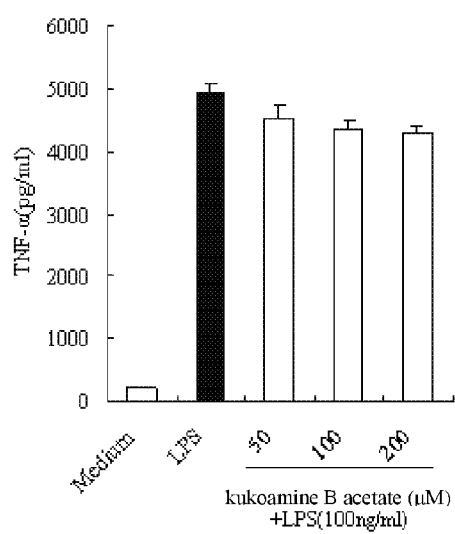
Figure 3:
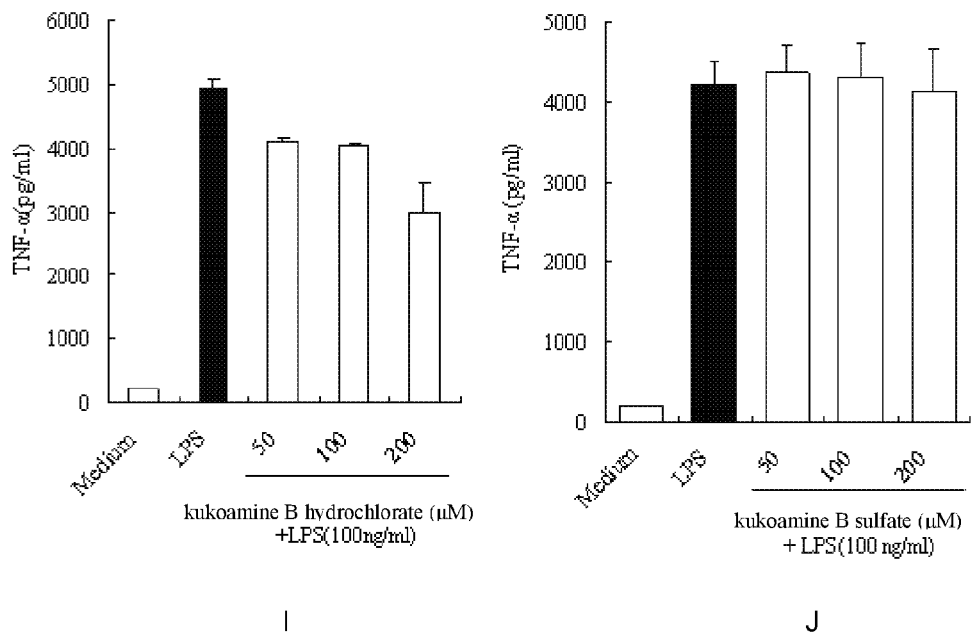

17.2 Results: Each of the salts of kukoamine B can inhibit the release of TNF-α, inflammatory mediators, in RAW264.7 cells induced by LPS, and the results are shown in FIG. 3, wherein: FIG. 3A is the result of kukoamine B malate; FIG. 3B is the result of kukoamine B succinate; FIG. 3C is the result of kukoamine B lactate; FIG. 3D is the result of kukoamine B tartrate; FIG. 3E is the result of kukoamine B methanesulfonate; FIG. 3F is the result of kukoamine B p-toluenesulfonate; FIG. 3G is the result of kukoamine B glutamate; FIG. 3H is the result of kukoamine B acetate; FIG. 3I is the result of kukoamine B hydrochlorate; and FIG. 3J is the results of kukoamine B sulfate.

EXAMPLE 18

The Test about the Inhibition of Salts of Kukoamine B on the Release of Inflammatory Mediators in RAW264.7 Cells Induced by CpG DNA 18.1 Methods: RAW264.7 cells are diluted to $1 \times 10^6$/ml in DMEM culture medium, added into a 96-well cell culture plate (200 μl per well), and incubated at 37° C. in a 5% $CO_2$ humidified incubator for 4 h, and then the supernatant is replaced with 200 μl of serum-free DMEM culture medium after cells attachment. Next, each well is added with CpG DNA (final concentration of 10 μg/ml), and then added with one of the salts of kukoamine B (including kukoamine B malate, kukoamine B succinate, kukoamine B lactate, kukoamine B tartrate, kukoamine B methanesulfonate, kukoamine B p-toluenesulfonate, kukoamine B glutamate, kukoamine B acetate, kukoamine B hydrochlorate, and kukoamine B sulfate) to obtain the final concentration of 0, 50, 100, and 200 μM, respectively. The control group contains no CpG DNA. Then, the incubation goes on for 4 h. The supernatant is collected to measure the concentration of TNF-α according to the manufacturer's instructions of ELISA kit.

Figure 4:
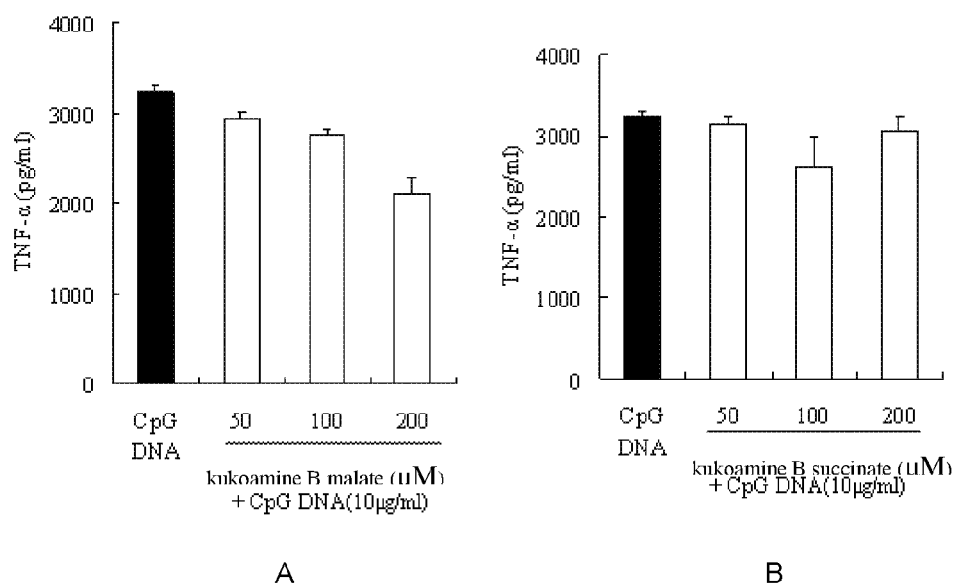
FIG. 4 shows the inhibition of salts of kukoamine B on the release of inflammatory mediators in RAW264.7 cells induced by CpG DNA.
Figure 4:
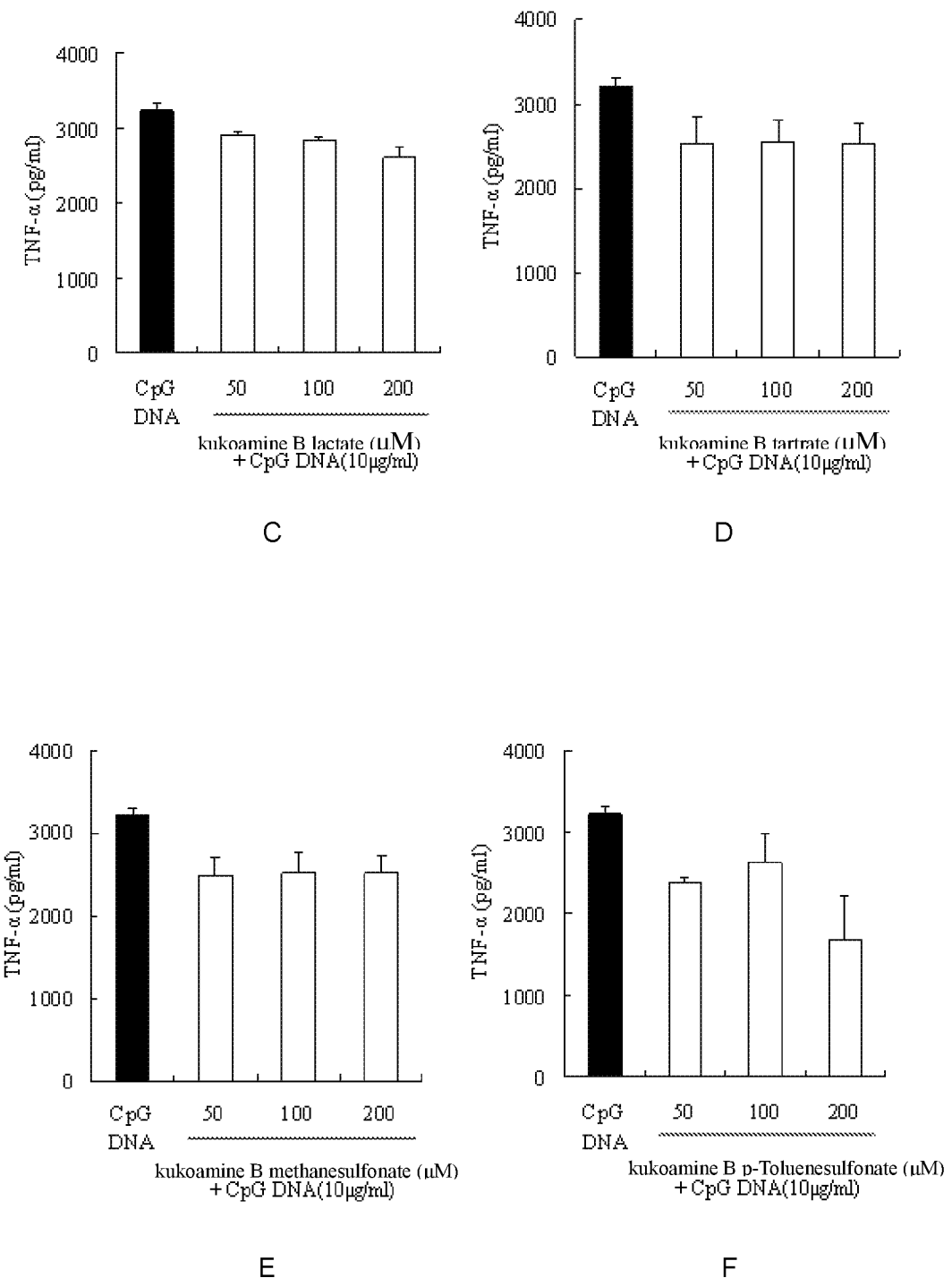

18.2 Results: Each of the salts of kukoamine B can inhibit the release of TNF-α, inflammatory mediators, in RAW264.7 cells induced by CpG DNA, and the results are shown in FIG. 4; wherein: FIG. 4A is the result of kukoamine B malate; FIG. 4B is the result of kukoamine B succinate; FIG. 4C is the result of kukoamine B lactate; FIG. 4D is the result of kukoamine B tartrate; FIG. 4E is the result of kukoamine B methanesulfonate; FIG. 4F is the result of kukoamine B p-toluenesulfonate; FIG. 4G is the result of kukoamine B glutamate; FIG. 4H is the result of kukoamine B acetate; FIG. 4I is the result of kukoamine B hydrochlorate; and FIG. 4J is the results of kukoamine B sulfate.

EXAMPLE 19

The Protective Effect of the Salts of Kukoamine B to the Sepsis Model of Mice.

19.1 Methods: 120 Balb/c mice, each of 19-21 g, half of which being male and half female, are divided into six groups randomly, including control group, antibiotic group, antibiotic and kukoamine B hydrochlorate group, antibiotic and kukoamine B methanesulfonate group, antibiotic and kukoamine B p-toluenesulfonate group, and antibiotic and kukoamine B benzene sulfonate group. Each group contains 20 mice. The mice are narcotized with anesthesia machine; the vapor concentration of isoflurane is 5%; the pressure of the mixed gas is 1 MPa; anesthesia time is about 5 min. The mice model are setup by cecal ligation and puncture (CLP) comprising the following steps: the mice are maintained in supine position, and the abdomen skin is disinfected with iodophor; the skin, muscular layer and peritoneum below the midpoint of linea alba 0.3 cm are cut open with ophthalmic scissors (the length of the incisions is 0.8 CM); the muscular layer is picked up with ophthalmic forceps, and the enterocoelia is explored with ophthalmic forceps; the cecum is pulled out and ligated with No. 4 suture at 0.5 CM from the end of cecum; then, the cecum is vertically punctured with No. 12 needle, and squeezed to extrude contents; finally, the cecum is put back and the incision is stitched. Thereafter, the mice in control group are injected with 0.2 ml of sterile saline through tail vein; the mice in antibiotic group are injected with antibiotic (ampicillin sodium-sulbactam sodium) at a dosage of 80 mg/kg body weight through tail vein at 4 hours after surgery; the mice in other four groups are separately injected with kukoamine B hydrochlorate, kukoamine B methanesulfonate, kukoamine B p-toluenesulfonate and kukoamine B benzene sulfonate at a dosage of 2.5 mg/kg body weight at a time through tail vein at 0, 4, 12, 20, 28, 36, 44, 52, 60 and 68 hours after surgery. The general status and mortality rate of mice are observed in 7 days after surgery, and the survival rates between control group and medicated group are compared.

Figure 5:
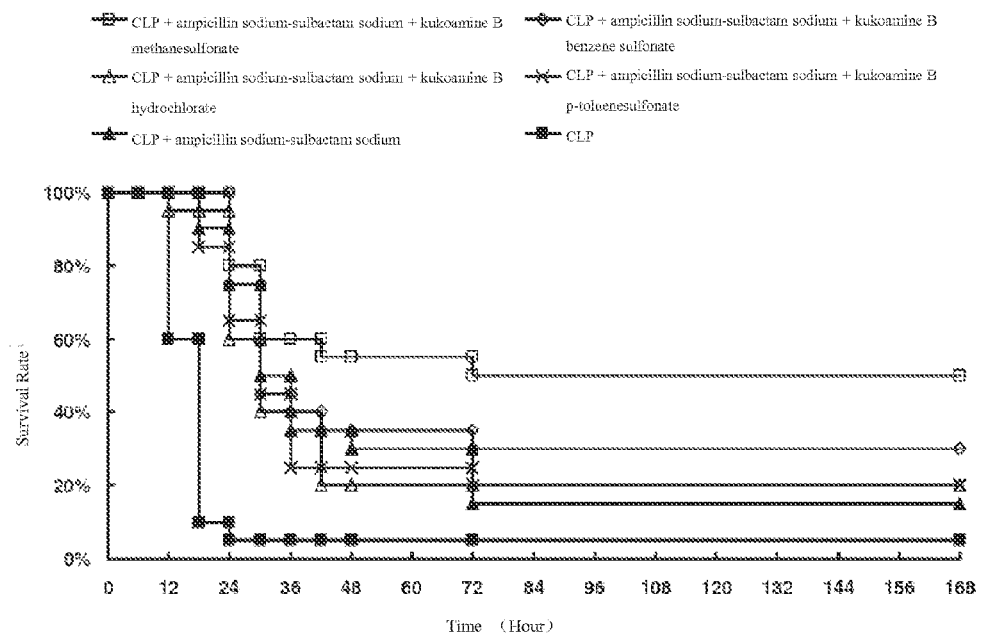
FIG. 5 shows the protective effect of the kukoamine B hydrochlorate, kukoamine B methanesulfonate, kukoamine B p-toluenesulfonate and kukoamine B benzene sulfonate to the sepsis model of mice, respectively.

19.2 Results: The mortality rate of CLP control group in 7 days is 95%. The survival rate of the mice treated with ampicillin sodium-sulbactam sodium (80 mg/kg) is 15%. When treated with the combination of salts of kukoamine B and antibiotic, kukoamine B hydrochlorate and kukoamine B p-toluenesulfonate could improve the survival rate of mice to 20%, kukoamine B benzene sulfonate could improve the survival rate of mice to 30%, and kukoamine B methanesulfonate could improve the survival rate of mice to 50%. The results indicate that kukoamine B hydrochlorate, kukoamine B methanesulfonate, kukoamine B p-toluenesulfonate and kukoamine B benzene sulfonate have protective effects to the sepsis model of mice, wherein kukoamine B methanesulfonate has the best effect. The results are shown in FIG. 5.

The invention claimed is:
1. A method for preparing the salts of kukoamine B, the method comprising:
(1) reacting compound I with hydrobromic acid at 100-160° C, to generate compound II, wherein a stoichiometric ratio of compound I to hydrobromic acid is 1:2-5,

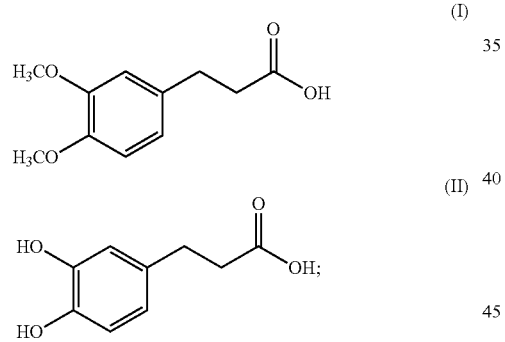

(2) dissolving compound II in N, N-dimethylformamide to make a reaction system in a N, N-dimethylformamide solution environment, and then adding potassium carbonate and benzyl chloride, wherein the reaction is carried out at 60-100° C. to generate compound III,

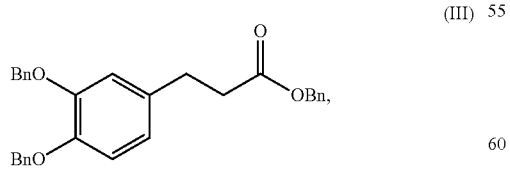

and
wherein a stoichiometric ratio of compound II:potassium carbonate:benzyl chloride is 1:3-6:3-5;
(3) adding compound III into sodium hydroxide solution, then adding methanol to make a reaction system in a methanol solution environment, wherein the reaction is carried out at 40-90° C. to generate compound IV,

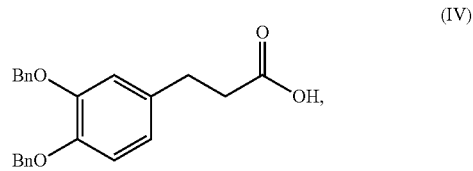 [SMILES: O=C(CCc1ccc(OCc2ccccc2)c(OCc2ccccc2)c1)OCc1ccccc1]

and
wherein a stoichiometric ratio of compound III to sodium hydroxide is 1:1-3;
(4) dissolving compound IV in dichloromethane, and then adding N, N-dimethylformamide to make a reaction system in an environment of a mixed solution containing N, N-dimethylformamide and dichloromethane, then adding thionyl chloride, wherein the reaction is carried out at 45-65° C. to generate compound V,

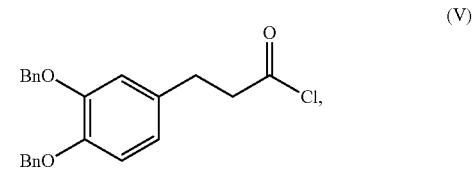 [SMILES: O=C(Cl)CCc1ccc(OCc2ccccc2)c(OCc2ccccc2)c1]

and
wherein a stoichiometric ratio of compound IV to thionyl chloride is 1:1-2;
(5) combining compound VI with sodium hydroxide solution, and then adding ethanol solution of Di-tert-butyl dicarbonate, wherein the reaction is carried out at room temperature to generate compound VII,

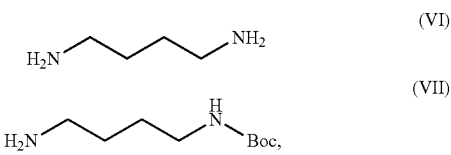

and
wherein a stoichiometric ratio of sodium hydroxide:compound VI:Di-tert-butyl dicarbonate is 1-2:1:0.5-1;
(6) dissolving compound VII in methanol to make a reaction system in a methanol solution environment, and then adding a methanol solution of acrylon, wherein the reaction is carried out at room temperature to generate compound VIII,

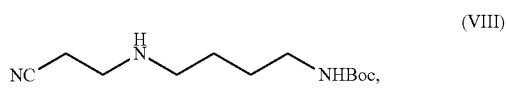

and
wherein a stoichiometric ratio of compound VII to acrylon is 1:1-2;
(7) combining compound VIII with tetrahydrofuran and triethylamine to make a reaction system in an environment of mixed solution containing tetrahydrofuran and triethylamine, and then adding a tetrahydrofuran solution of benzyl chloroformate wherein the reaction is carried out at room temperature to generate compound IX,

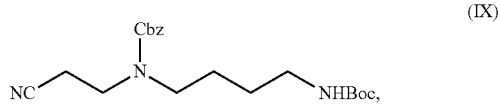 [SMILES: CC(C)(C)OC(=O)NCCCCN(CCC#N)C(=O)OCc1ccccc1]

and
wherein a stoichiometric ratio of compound VIII to benzyl chloroformate is 1:1-2;
(8) placing compound IX into an autoclave, and adding saturated methanol solution of ammonia until compound IX is completely dissolved and then adding Raney nickel, a mass of which is equivalent to 10-50% of the compound IX, into the reaction solution, wherein aeration is applied to ensure the reaction system in hydrogen under 1-10 MPa, and wherein the reaction is carried out at 35-50° C. to generate compound X,

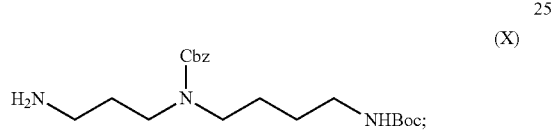

(9) dissolving compound X in dichloromethane, and then adding triethylamine to make a reaction system in an environment of mixed solution containing dichloromethane and triethylamine, then adding the dichloromethane solution of compound V into a reaction solution at a temperature below 0° C., wherein the reaction generates compound XI,

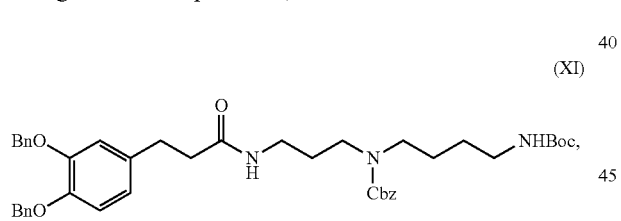

and
wherein a stoichiometric ratio of compound X to compound V is 1:1-1.5;
(10) dissolving compound XI in dichloromethane to make a reaction system in a dichloromethane environment, and then adding trifluoroacetic acid wherein the reaction is carried out at room temperature to generate compound XII,

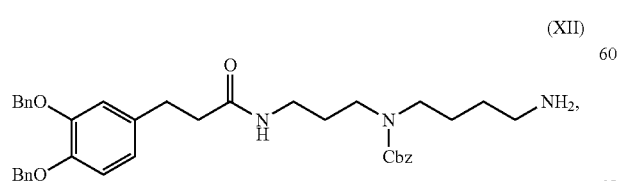

and wherein a stoichiometric ratio of compound XI to trifluoroacetic acid is 1:2-5;
(11) dissolving compound XII in methanol, and then adding triethylamine to make a reaction system in an environment of mixed solution containing methanol and triethylamine, heating the reaction system to 50-80° C. and adding methanol solution of acrylon, cooling the reaction solution down to room temperature to carry out the reaction, which generates compound XIII,

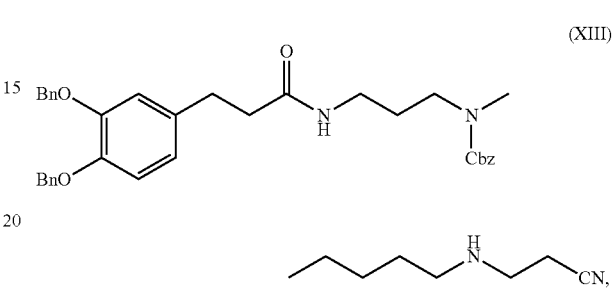

wherein a stoichiometric ratio of compound XII to acrylon is 1:1-2;
(12) dissolving compound XIII in dichloromethane, and then adding triethylamine to make a reaction system in an environment of mixed solution containing dichloromethane and triethylamine, adding the dichloromethane solution of compound V into the reaction system at a temperature below 0° C., wherein the reaction generates compound XIV,

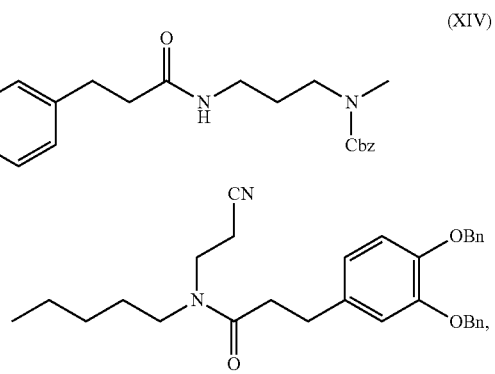

and
wherein a stoichiometric ratio of compound XIII to compound V is 1:1-1.5;
(13) placing compound XIV into an autoclave, and adding mixed solution containing saturated methanol solution of ammonia and tetrahydrofuran until compound XIV is completely dissolved, such that the reaction system is in environment of solution thereof, and then adding Raney nickel, the mass of which is equivalent to 10-50% of the compound XIV, into the reaction system, wherein aeration is applied to ensure the reaction system in hydrogen under 1-10MPa, wherein the reaction is carried out at 35-50° C. to generate compound XV,

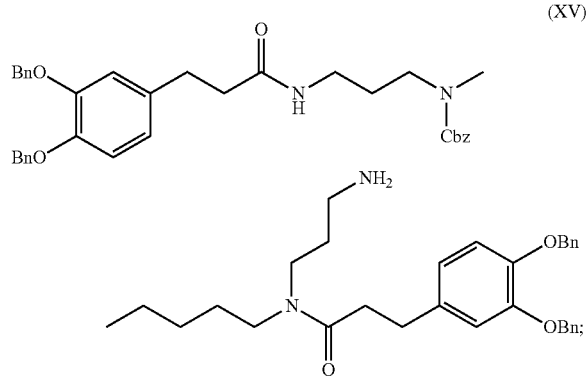 (XV)

and

(14) placing, into an autoclave, compound XV and an inorganic acid including at least one of a hydrogenacid and an oxacid, or an organic acid including at least one of a carboxylic acid, hydroxy acid, sulfoacid and acidic amino acid, and adding a mixed solution containing methanol, tetrahydrofuran and water until compound XV is completely dissolved, such that a reaction system is in an environment of solution thereof, and then adding a palladium-carbon catalyst, the mass of which is equivalent to 10-30% of the compound XV, into the reaction system, wherein aeration is applied to ensure the reaction system in hydrogen under 1-10MPa, wherein the reaction is carried out at 25-45° C. to generate salt of kukoamine B, wherein a stoichiometric ratio of compound XV to acid is 1:1-8, the salt of kukoamine B having the chemical structure:

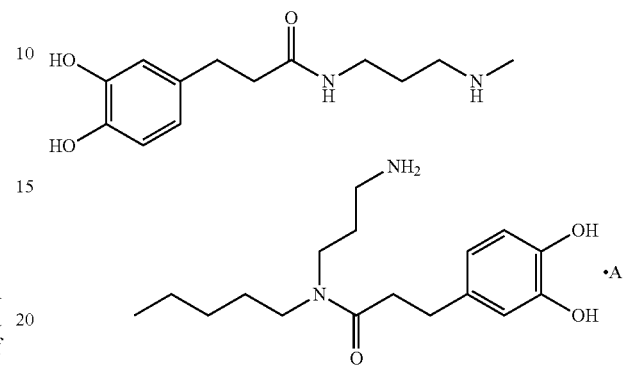

wherein A comprises an inorganic acid including at least one of a hydrogenacid and oxacid, or an organic acid including at least one of carboxylic acid, hydroxy acid, sulfoacid and acidic amino acid.

\* \* \* \* \*